(12) United States Patent
Nakasugi et al.

(10) Patent No.: US 11,366,389 B2
(45) Date of Patent: Jun. 21, 2022

(54) ALLYLOXY DERIVATIVE, RESIST UNDERLAYER FORMING COMPOSITION USING THE SAME, AND METHOD OF MANUFACTURING RESIST UNDERLAYER AND SEMICONDUCTOR DEVICE USING THE SAME

(71) Applicant: Merck Patent GmbH, Darmstadt (DE)

(72) Inventors: Shigemasa Nakasugi, Yamato (JP); Hiroshi Yanagita, Kakegawa (JP); Takashi Sekito, Kakegawa (JP); Yusuke Hama, Kakegawa (JP); Yuriko Matsuura, Kakegawa (JP)

(73) Assignee: MERCK PATENT GMBH, Darmstadt (DE)

( * ) Notice: Subject to any disclaimer, the term of this patent is extended or adjusted under 35 U.S.C. 154(b) by 173 days.

(21) Appl. No.: 16/760,908

(22) PCT Filed: Oct. 30, 2018

(86) PCT No.: PCT/EP2018/079621
§ 371 (c)(1),
(2) Date: May 1, 2020

(87) PCT Pub. No.: WO2019/086402
PCT Pub. Date: May 9, 2019

(65) Prior Publication Data
US 2021/0181636 A1    Jun. 17, 2021

(30) Foreign Application Priority Data

Nov. 1, 2017 (JP) .............................. JP2017-212054

(51) Int. Cl.
*G03F 7/11* (2006.01)
*C08G 61/02* (2006.01)
(Continued)

(52) U.S. Cl.
CPC .............. *G03F 7/11* (2013.01); *C07C 43/215* (2013.01); *C08G 61/02* (2013.01); *C09D 149/00* (2013.01);
(Continued)

(58) Field of Classification Search
CPC .............. C07C 2603/24; C07C 43/215; C07C 2601/14; C07C 2603/18; C08G 2261/124;
(Continued)

(56) References Cited

U.S. PATENT DOCUMENTS 8,426,111 B2   4/2013   Takei et al.
8,952,121 B2   2/2015   Paulasaari
(Continued)

FOREIGN PATENT DOCUMENTS

EP      3141959 A1    3/2017
JP   2009051780 A    3/2009
(Continued)

OTHER PUBLICATIONS

International Search Report for PCT/EP2018/079621 dated Feb. 13, 2019.
(Continued)

*Primary Examiner* — Caleen O Sullivan
(74) *Attorney, Agent, or Firm* — Faegre Drinker Biddle & Reath LLP

(57) ABSTRACT

The present invention provides a resist underlayer forming composition, which is well in heat resistance and gap filling. Further, the present invention provides methods of manufacturing a resist underlayer and semiconductor device using it. [Means for Solution] A composition comprising a allyloxy derivative having a specific group and a solvent, and methods of manufacturing a resist underlayer and semiconductor device using it.

20 Claims, 1 Drawing Sheet

(b)

(51) Int. Cl.
*C07C 43/215* (2006.01)
*C09D 149/00* (2006.01)
*H01L 21/027* (2006.01)
*H01L 21/311* (2006.01)
*H01L 21/768* (2006.01)

(52) U.S. Cl.
CPC .... *H01L 21/0274* (2013.01); *H01L 21/31111* (2013.01); *H01L 21/31144* (2013.01); *H01L 21/76802* (2013.01); *H01L 21/76877* (2013.01); *C07C 2601/14* (2017.05); *C07C 2603/18* (2017.05); *C07C 2603/24* (2017.05); *C08G 2261/124* (2013.01); *C08G 2261/148* (2013.01); *C08G 2261/1424* (2013.01); *C08G 2261/226* (2013.01); *C08G 2261/228* (2013.01); *C08G 2261/312* (2013.01); *C08G 2261/3142* (2013.01)

(58) Field of Classification Search
CPC ...... C08G 2261/1424; C08G 2261/148; C08G 2261/226; C08G 2261/228; C08G 2261/312; C08G 2261/3142; C08G 61/02; G03F 7/094; G03F 7/091; G03F 7/11; C09D 149/00; H01L 21/0274; H01L 21/31111; H01L 21/31144; H01L 21/76802; H01L 21/76877

USPC ....................................... 430/270.1; 438/637
See application file for complete search history.

(56) References Cited

U.S. PATENT DOCUMENTS

| 10,550,068 | B2 | 2/2020 | Echigo |
| 2017/0144954 | A1* | 5/2017 | Makinoshima ....... C07C 321/26 |
| 2017/0154782 | A1 | 6/2017 | Nakafuji et al. |

FOREIGN PATENT DOCUMENTS

| JP | 4998261 B2 | 8/2012 |
| JP | 5120577 B2 | 1/2013 |
| JP | 5794228 B2 | 10/2015 |
| WO | WO-2017014284 A1 | 1/2017 |

OTHER PUBLICATIONS

Written Opinion of the International Searching Authority for PCT/EP2018/079621 dated Feb. 13, 2019.

* cited by examiner

ALLYLOXY DERIVATIVE, RESIST UNDERLAYER FORMING COMPOSITION USING THE SAME, AND METHOD OF MANUFACTURING RESIST UNDERLAYER AND SEMICONDUCTOR DEVICE USING THE SAME

CROSS-REFERENCE TO RELATED APPLICATIONS

This application is a national stage application (under 35 U.S.C. § 371) of PCT/EP2018/079621, filed Oct. 30, 2018, which claims benefit of Japanese Application No. 2017-212054, filed Nov. 1, 2017, both of which are incorporated herein by reference in their entirety.

BACKGROUND OF THE INVENTION

Technical Field

The present invention relates to an allyloxy derivative and a resist underlayer forming composition using the same. The present invention also relates to methods of manufacturing the resist underlayer and semiconductor device using the resist underlayer forming composition.

Background Art

In the process of manufacturing devices such as semiconductors, microfabrication by lithography technology using a photoresist (hereinafter also referred to as resist) has been generally performed. The microfabrication process comprises the steps of: forming a thin resist layer on a semiconductor substrate such as a silicon wafer, covering the layer with a mask pattern corresponding to a desired device pattern, irradiating the layer with an active light such as ultraviolet radiation through the mask pattern, developing the exposed layer to obtain a resist pattern, and etching the substrate or the like using the obtained resist pattern as a protective film, whereby a fine unevenness corresponding to the above-described pattern is formed. According to the recent development of high-density integration and three-dimensional integration of semiconductors, it has been requested to form further another layer on a substrate processed to form a fine unevenness, and to repeat the processing.

A resist layer or another film can be coated on such a substrate in a state of solution and cured by radiation or heating to form a film. The resist layer and the other film are laminated in such a precise environment, and characteristics such as respective film forming properties and not being intermixed with other layer are required.

Under such circumstances, a study focusing on a compound containing a specific carbon-carbon double bond has been conducted in order to obtain a resist underlayer having high elastic modulus and etching resistance while maintaining the effect of preventing the generation of a standing wave (Patent document 1). Further, a study focusing on a resist underlayer that can be formed by means of light irradiation due to the inclusion of a polymerizable compound comprising at least one radical polymerizable ethylenically unsaturated bond has been conducted (Patent document 2). Further, a study focused on novolac resin having good oxidative thermal stability has been conducted (Patent document 3). Further, a study focused on specific compounds has been conducted to provide a resist composition which is sensitive also to radiation, and evaluation or the like of film formability on a flat silicon wafer has been carried out (Patent document 4).

PRIOR ART DOCUMENTS

Patent Documents

[Patent document 1] JP 5794228 B
[Patent document 2] JP 5120577 B
[Patent document 3] US 8952121 B
[Patent document 4] JP 4998261 B

SUMMARY OF THE INVENTION

Problems to be Solved by the Invention

The present inventors considered that the resist underlayer in the lithography process was useful when it possesses good heat resistance. The present inventors considered that a compound, of which decomposition or the like was not generated and weight was not decreased in an environment exposed to high temperature such as that gradually rising in temperature for a long time, was useful for a resist underlayer. Further, the present inventors considered that it was also useful for the process if the decrease in film thickness can be suppressed when being baked at high temperature. In a complicated and finely processed substrate (for example, a stepped substrate), structures existing on an upper surface of the substrate (walls and holes) may not be uniformly distributed and may be unevenly distributed in the state of coarse/dense. The present inventors considered that gap filling was possible even in such a substrate and that it was desirable in the semiconductor manufacturing process that the upper surface of the formed film was flat.

By the intensive study based on the idea as described above, the present inventors found an allyloxy derivative to be described later and a resist underlayer forming composition containing the same. Further, curing of these compositions can be promoted by a predetermined ultraviolet radiation, and it is possible to reduce the additive components.

Further, the present inventors found that damage to other organic layers due to heating can be suppressed and they were useful in the lamination process.

Means for Solving the Problems

The resist underlayer forming composition according to the present invention comprises:
an allyloxy derivative comprising a group X represented by the following formula (1):

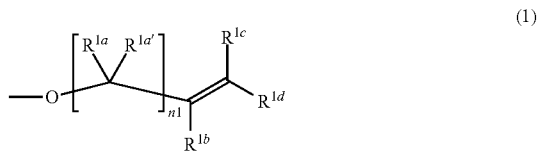

wherein,
$R^{1a}$ and $R^{1a'}$ are each independently hydrogen, or linear or branched $C_{1-4}$ alkyl,
$R^{1b}$, $R^{1c}$, and $R^{1d}$ are each independently hydrogen, or linear or branched $C_{1-4}$ alkyl, and
n1 is 1, 2, or 3; and
a solvent.

The method of manufacturing a resist underlayer according to the present invention comprises:
applying the above-mentioned composition above a substrate to form a resist underlayer forming composition layer; and
curing said resist underlayer forming composition layer.

The "above a substrate" includes the case where the resist underlayer is formed, in contact with a substrate, on the substrate and the case where it is formed via another layer. For example, it is one embodiment of the present invention to form a planarization film on a substrate in contact with the substrate, and to manufacture a resist underlayer of the present invention on the planarization film. In this example, the resist underlayer is manufactured, via another layer (planarization film), above the substrate.

The method of manufacturing a semiconductor device according to the present invention comprises:
manufacturing the resist underlayer according to the above-mentioned method;
applying a resist composition above said resist underlayer to form a resist composition layer;
exposing said resist composition layer;
developing said resist composition layer after the exposure to form a resist pattern;
etching with said resist pattern as a mask; and
processing the substrate.

The formation of a resist composition layer above a resist underlayer includes the case where the resist composition layer is formed, in contact with the underlayer, directly thereon and the case where the layer is indirectly formed via another layer being on the underlayer. For example, it is an embodiment of the present invention to form a BARC layer, in contact with the resist underlayer, on the resist underlayer, and to manufacture a resist composition layer on the BARC layer. In this example, the resist composition layer is manufactured, via another layer (BARC layer), above the resist underlayer.

The allyloxy derivative according to the present invention comprises three or more group X represented by the following formula (1):

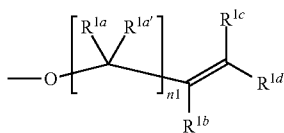

(1)

wherein,
$R^{1a}$ and $R^{1a'}$ are each independently hydrogen, or linear or branched $C_{1-4}$ alkyl,
$R^{1b}$, $R^{1c}$, and $R^{1d}$ are each independently hydrogen, or linear or branched $C_{1-4}$ alkyl, and
n1 is 1, 2, or 3.

Effects of the Invention

The resist underlayer formed from the composition of the present invention is capable filling gap even on a processed substrate and having high film planarity. Further, when the temperature is raised after the film formation, it can have low weight reduction rate, low film thickness reduction rate and/or good heat resistance. Further, the present composition is useful in the lamination process, because curing of the present composition can be promoted by irradiation of ultraviolet radiation, damage to other layers can be suppressed, and the like.

DETAILED DESCRIPTION OF THE INVENTION

Mode for Carrying Out the Invention

Figure 1:
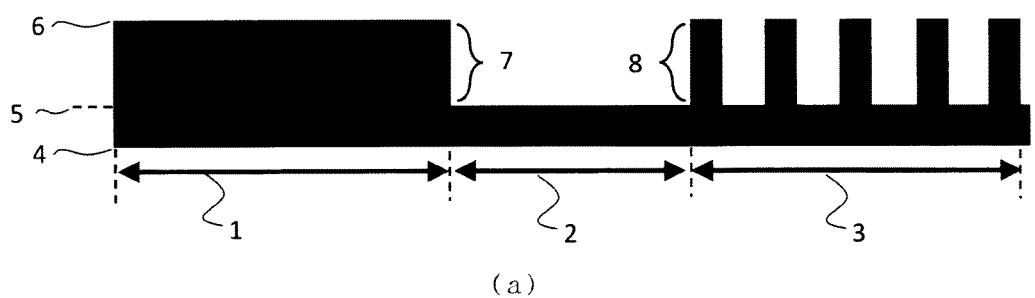
FIG. 1: Explanatory drawing of the structure of a substrate used for planarity evaluation

Hereinafter, symbols, units, abbreviations, and terms have the following meanings in the present specification unless otherwise specified.

In the present specification, when numerical ranges are indicated using "-" or "to", they include both end points, and the units thereof are common. For example, 5-25 mol % means 5 mol % or more and 25 mol % or less.

In the present specification, the hydrocarbon means one including carbon and hydrogen, and optionally including oxygen or nitrogen. The hydrocarbyl group means a monovalent or divalent or higher hydrocarbon.

In the present specification, the aliphatic hydrocarbon means a linear, branched or cyclic aliphatic hydrocarbon, and the aliphatic hydrocarbon group means a monovalent or divalent or higher valent aliphatic hydrocarbon. The aromatic hydrocarbon means a hydrocarbon containing an aromatic hydrocarbon ring which may not only comprise an aliphatic hydrocarbon group as a substituent but also be optionally condensed with an aliphatic hydrocarbon ring. The aromatic hydrocarbon group means a monovalent or divalent or higher valent aromatic hydrocarbon. These aliphatic hydrocarbon groups and aromatic hydrocarbon groups optionally contain fluorine, oxy, hydroxy, amino, carbonyl, or silyl and the like. Further, the aromatic hydrocarbon ring means a hydrocarbon comprising a conjugated unsaturated ring structure, and the aliphatic hydrocarbon ring means a hydrocarbon comprising a ring structure but no conjugated unsaturated ring structure.

In the present specification, the description such as "$C_{x-y}$", "$C_x$-$C_y$" and "$C_x$" means the number of carbons in the molecule or substituent group. For example, $C_{1-6}$ alkyl means alkyl (such as methyl, ethyl, propyl, butyl, pentyl and hexyl) having 1 to 6 carbons. The fluoroalkyl as used in the present specification refers to one in which one or more hydrogens in alkyl is replaced with fluorine, and the fluoroaryl is one in which one or more hydrogens in aryl are replaced with fluorine.

In the present specification, when a polymer comprises a plural type of repeating units (structural units), these repeating units are copolymerized. These copolymerization are any of alternating copolymerization, random copolymerization, block copolymerization, graft copolymerization, or a mixture thereof.

In the present specification, "%" represents mass % and "ratio" represents ratio by mass.

In the present specification, Celsius is used as the temperature unit. For example, 20 degrees means 20 degrees Celsius.

[Resist Underlayer Forming Composition]

The resist underlayer forming composition of the present invention (hereinafter, sometimes referred to as "the composition" for simplicity) is good when used in the manufacture of a pattern using a lithography technique. The composition comprises an allyloxy derivative and a solvent.

Here, in the present invention, the resist underlayer means a carbon-containing film to be formed between a substrate and a resist layer, and functions as a planarization layer, an adhesion layer, a spin on carbon layer (SOC layer), a bottom anti-reflective coating (BARC layer), or a hard mask layer. The resist underlayer according to the present invention may also combines these functions and, for example, it may function as both a planarization layer and a BARC layer. The resist underlayer according to the present invention may be formed between a substrate and a resist layer and does not need to come in contact with the resist layer.

[Allyloxy Derivative]

The allyloxy derivative according to the present invention is one comprising a group X represented by the following formula (1), preferably comprising three or more group X, more preferably four or more group X. The allyloxy derivative of the present invention may comprise a structure containing a plurality of structural units. For example, it may be a polymer.

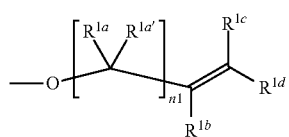
(1)

wherein,
$R^{1a}$ and $R^{1a'}$ are each independently hydrogen, or linear or branched $C_{1-4}$ alkyl,
$R^{1b}$, $R^{1c}$, and $R^{1d}$ are each independently hydrogen, or linear or branched $C_{1-4}$ alkyl, and
n1 is 1, 2 or 3.

Furthermore, the allyloxy derivative in the present invention means a compound comprising a group X.

In the case of comprising a plurality of group X, they may be identical to or different from each other.

$R^{1a}$ and $R^{1a'}$ are preferably selected from the group consisting of hydrogen, methyl, ethyl, isopropyl and butyl, more preferably selected from the group consisting of hydrogen and methyl, and further preferably both are hydrogen.

$R^{1b}$, $R^{1c}$, and $R^{1d}$ are preferably selected from the group consisting of hydrogen, methyl, ethyl, isopropyl and butyl, more preferably selected from the group consisting of hydrogen and methyl, and further preferably all are hydrogen.

n1 is preferably 1.

The portion other than the group X constituting the allyloxy derivative according to the present invention is preferably selected from linear or branched alkyl, a saturated hydrocarbon ring, an aromatic hydrocarbon ring, or any combination of any of these. Preferred embodiment of the portion other than the group X includes the following structures.

A combination of aromatic hydrocarbon rings

A combination of linear or branched (more preferably linear) alkyl and an aromatic hydrocarbon ring A combination of linear or branched (more preferably linear) alkyl and a saturated hydrocarbon ring A combination of linear or branched (more preferably branched) alkyl, an aromatic hydrocarbon ring and a saturated hydrocarbon ring The embodiment that the group X is bonded to the phenyl group in the portion other than the group X is preferred. Said phenyl group may be substituted with one or more, linear or branched alkyl (preferably methyl) or phenyl and may be unsubstituted.

Said linear or branched alkyl is preferably $C_{1-4}$, more preferably $C_{1-3}$. Said saturated hydrocarbon ring is preferably a cyclopentane ring or a cyclohexane ring, more preferably a cyclohexane ring. Said aromatic hydrocarbon ring is preferably a benzene ring, a naphthalene ring, a fluorene ring or an anthracene ring, more preferably a benzene ring, a fluorene ring or an anthracene ring.

The number of carbon atoms of the portion other than the group X is preferably 6 or more, more preferably 10 or more, further preferably 30 or more, still more preferably 39 or more. Further, the number of carbon atoms in the portion other than the group X is preferably 70 or less, more preferably 60 or less, further preferably 50 or less.

Here, in the present invention, when a plurality of group X is present, the number of carbon atoms in the portion other than the group X means the number of carbon atoms excluding that in all the group X. Further, the number of carbon atoms in the portion other than the group X means the number of carbon atoms in the portion other than the group X in one structural unit containing the group X when the allyloxy derivative contains a plurality of structural units.

For example, the allyloxy derivative shown at the lower left comprises four group X, and the portion other than X is $C_{39}$ and a combination of branched alkyl, aromatic hydrocarbon rings and saturated hydrocarbon rings. Further, the allyloxy derivative shown at the lower right comprises six group X, and the portion other than X is $C_{47}$ and a combination of linear or branched alkyl and aromatic hydrocarbon rings.

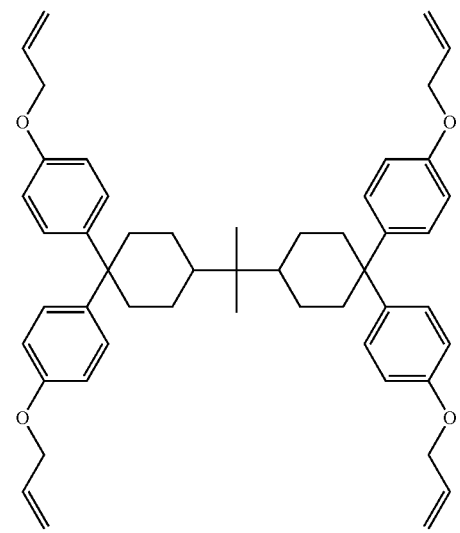

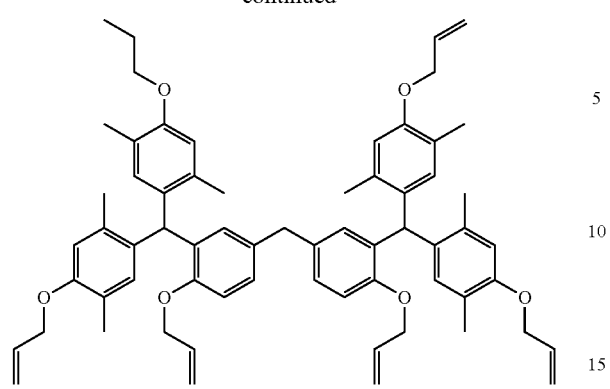
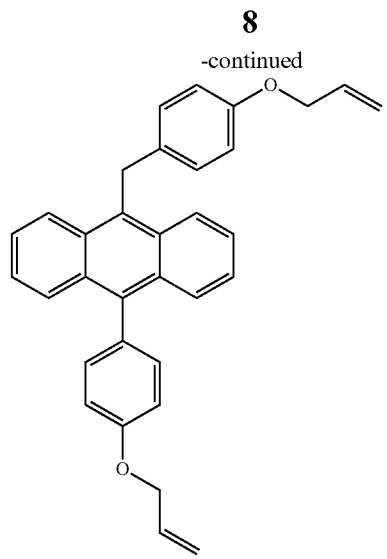
Specific examples of the allyloxy derivative are given below for understanding but are not intended to limit the present invention.
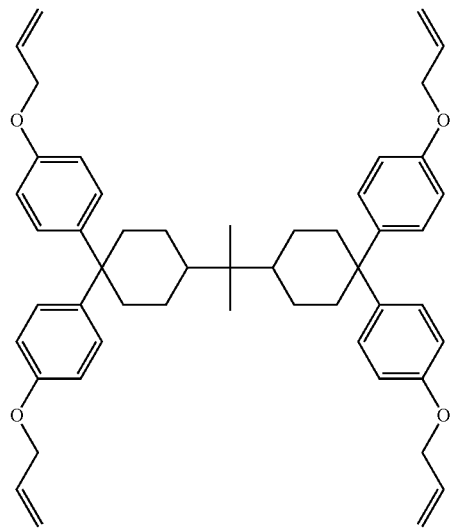
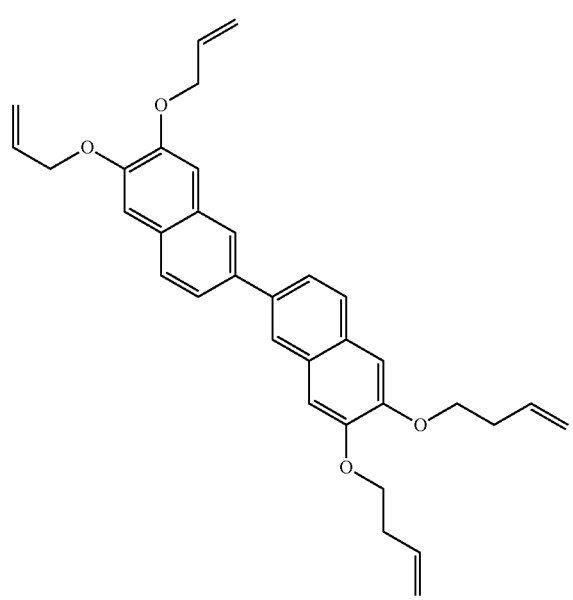
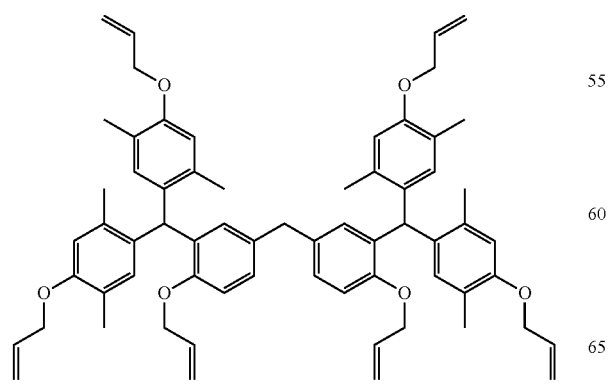
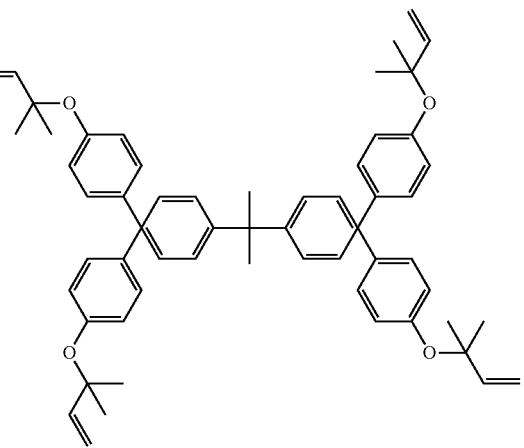

-continued

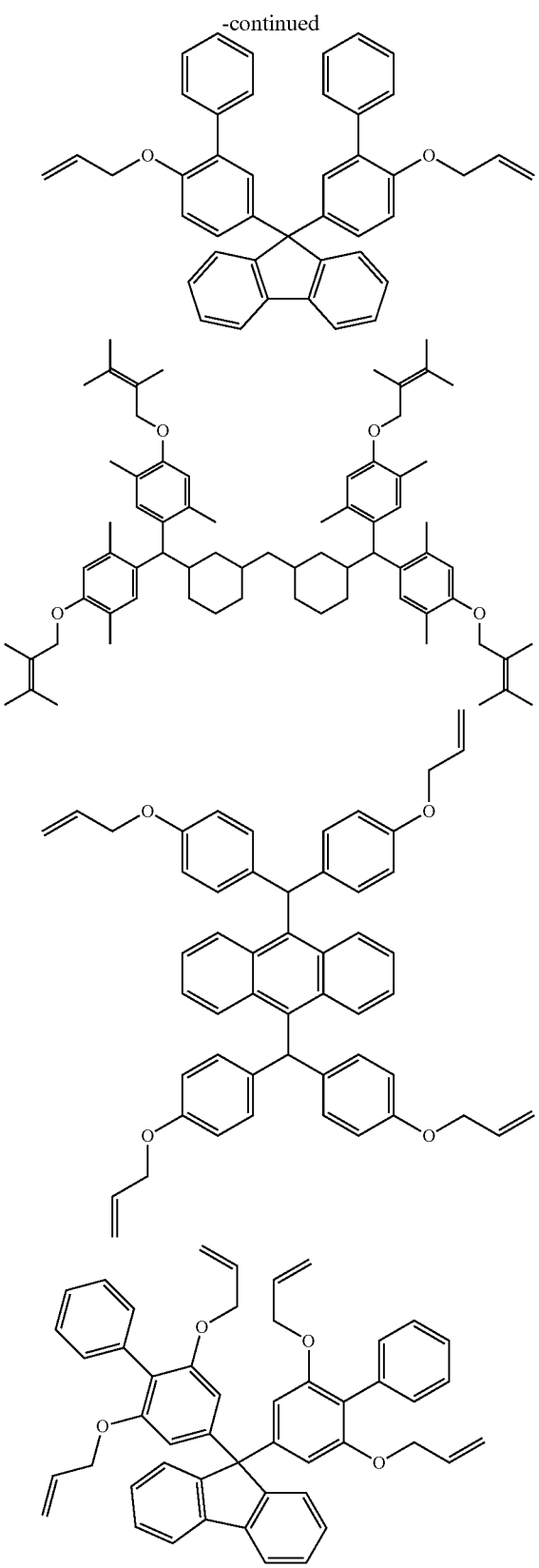

It is preferable that the allyloxy derivative according to the present invention comprises a structural unit represented by the following formula (2). The allyloxy derivative comprising the structural unit of the formula (2) may contain one or more structural units of the formula (2). In the allyloxy derivative contained in the present composition, the number of the structural unit of the formula (2) is not necessarily fixed to one. For example, an allyloxy derivative composed of one structural unit of the formula (2) and an allyloxy derivative composed of a plurality of the structural unit may be mixed.

$$-\left[Ar^{2a}-\left[X\right]_{n2}\right]-\quad (2)$$

wherein, $Ar^{2a}$ is a $C_{6-40}$ aromatic hydrocarbon group, n2 is 1, 2, 3, or 4, and X is as defined above and when n2 is 2, 3, or 4, X can be identical to or different from each other.

Preferably, $Ar^{2a}$ is phenyl, naphthyl, anthracene, fluorene, 9,9-diphenylfluorene, 9,9-dinaphthylfluorene, phenanthrene, or chrysene. More preferably, $Ar^{2a}$ is phenyl, naphthyl, anthracene, 9,9-diphenylfluorene, or 9,9-dinaphthylfluorene.

n2 is preferably 1 or 2, more preferably 2.

Preferred specific examples of the structural unit represented by the formula (2) are provided below.

(2)-1

(2)-2

(2)-3 wherein, p is 1, or 2 q and r are each 0, 1, or 2, with the proviso that q+r=1 or 2 s, t and u are each 0, 1, or 2, with the proviso that s+t+u=1, 2, or 3.

(2)-4

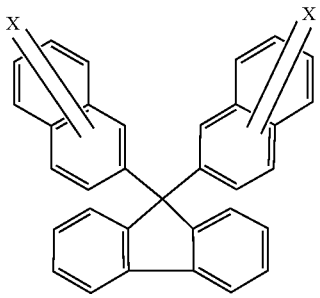

(2)-5

In addition, when the allyloxy derivative comprising the structural unit represented by the formula (2) is a polymer, it is preferable that none or few secondary carbon atom and the tertiary carbon atom are contained in the main chain of the polymer from the viewpoint of increasing the heat resistance of the resist underlayer to be formed from the derivative. In one embodiment of the present invention, the allyloxy derivative comprising the structural unit represented by the formula (2) is a polymer, and when synthesizing the polymer, the amount of the aldehyde derivative (formaldehyde or the like) is preferably 0-30 mol %, more preferably 0-15 mol %, further preferably 0-5 mol %, and still more preferably 0 mol %, based on all the components to be used for the synthesis. In order to obtain a polymer, in the main chain of which none or few of secondary carbon atom and tertiary carbon atom is contained, it is one of the preferred embodiments of the present invention to use a ketone derivative.

Further, among the structural units represented by the formula (2), a preferable embodiment is a structural unit represented by the following formula (3).

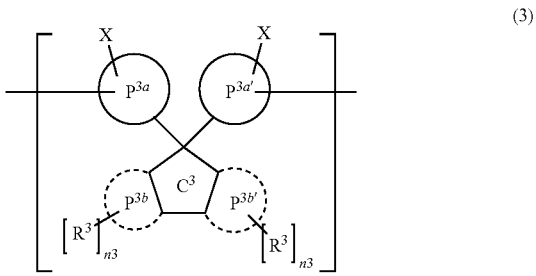

(3)

wherein,
$P^{3a}$ and $P^{3a'}$ are each independently a $C_{6-10}$ aromatic hydrocarbon ring,
$P^{3b}$ and $P^{3b'}$ are each independently a $C_{6-10}$ aromatic hydrocarbon ring and each of said $P^{3b}$ and $P^{3b'}$ contains two adjacent carbon atoms in $C^3$ as constitution atoms,
$R^3$ is each independently $C_{1-6}$ alkyl, halogen, or cyano,
n3 is each independently 0, 1, 2, 3, or 4, and
X is as defined above and can be identical to or different from each other.

$P^{3a}$ and $P^{3a'}$ are preferably each independently phenyl or naphthyl, more preferably phenyl.

$P^{3b}$ and $P^{3b'}$ are preferably each independently methyl, ethyl, isopropyl, butyl, fluorine or cyano, more preferably methyl or fluorine.

n3 is preferably 0.

For example, the compound shown at the lower left is an allyloxy derivative composed only of one structural unit of the formula (2). Further, the same structural unit is also represented by the formula (3). When an explanation is provided on the formula (3), $P^{3a}$, $P^{3a'}$, $P^{3b}$ and $P^{3b'}$ are phenyl and n3 are both 0. Since one structural unit is present, the connections with other structural units indicated by the arrows at the lower right are not used.

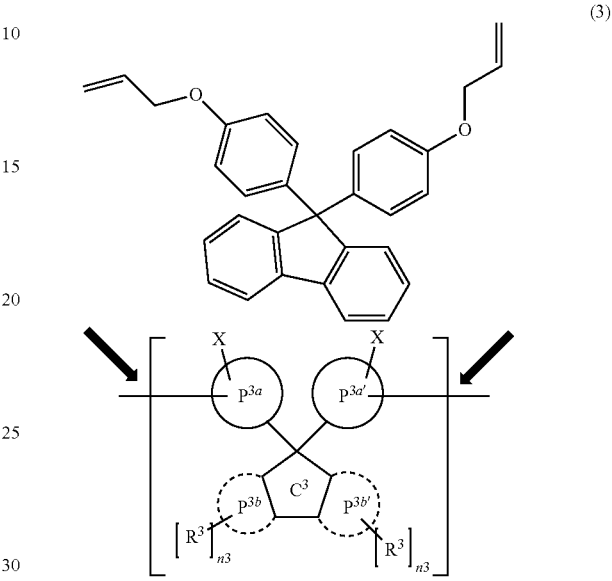

Preferred specific examples of the structural unit represented by the formula (3) are the above-mentioned formulas (2)-4 and (2)-5, more preferably the formula (2)-4.

The allyloxy derivative of the present invention preferably further comprises a structural unit represented by the following formula (4):

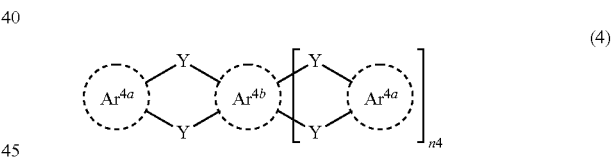

(4)

wherein,
$Ar^{4a}$ and $Ar^{4b}$ are each independently a $C_{6-10}$ aromatic hydrocarbon ring and each $Ar^{4a}$ can be identical to or different from each other,
n4 is 0, 1, or 2,
Y is each independently a single bond or $C_{1-9}$ alkylene, and at least one Y contained in the formula is a substituted methylene group which bonds to the other portion of the allyloxy derivative, and
with the proviso that $Ar^{4a}$ and $Ar^{4b}$ are not bonded with each other by two single bonds.

$Ar^{4a}$ and $Ar^{4b}$ are preferably a benzene ring or a naphthalene ring, and more preferably a benzene ring.

n4 is preferably 0 or 1, more preferably 0.

At least one Y is a substituted methylene group which bonds to the other portion of the allyloxy derivative. Here, said "other portion of the allyloxy derivative" does not include the structural units of one formula (4) containing said Y. However, when the allyloxy derivative contains a plurality of structural unit of the formula (4), the substituted methylene group being Y may bond to the other structural unit of the formula (4) (not the structural unit of the formula (4) in which itself is contained). Further, the substituted methylene group being Y may bond to the other portion than the group X contained in the structural unit of the formula (2). The substituted methylene group being Y does not bond to the group X contained in the structural unit of the formula (2).

Preferred specific examples of the structural unit represented by the formula (4) are provided below.

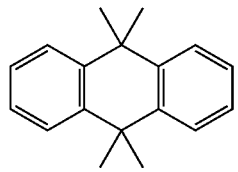

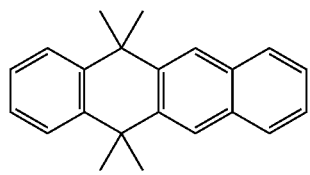

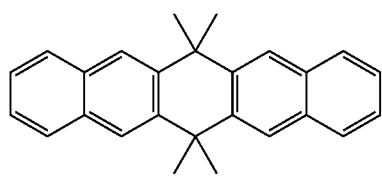

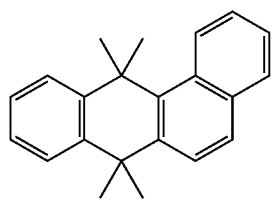

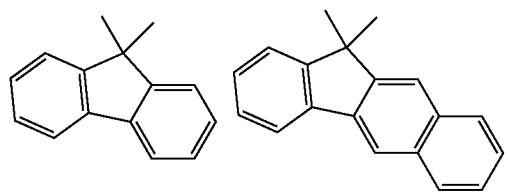

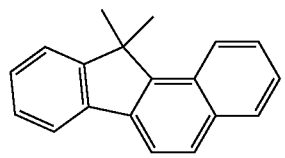

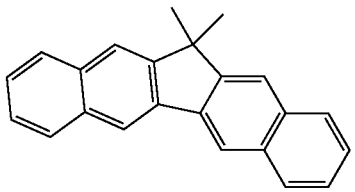

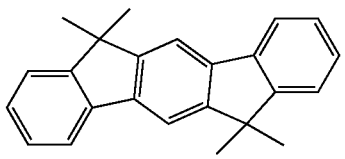

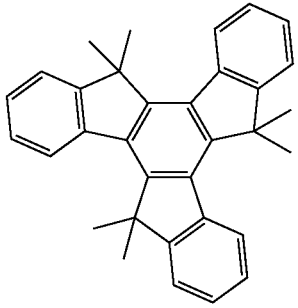

For example, the following structure is a structural unit represented by the formula (4), three Y are substituted methylene groups which are bonded to the other portions of the allyloxy derivative, and the other three Y are single bonds. $Ar^{4a}$ and $Ar^{4b}$ are benzene rings. n4 is 2, and two units surrounded by parentheses are bonded to the central $Ar^{4b}$ (benzene ring).

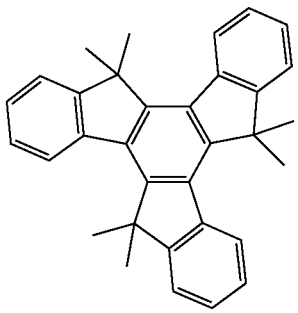 [SMILES: CC1(C)c2ccccc2-c2c1c1c(c3c2C(C)(C)c2ccccc2-3)C(C)(C)c2ccccc2-1]

A preferable embodiment of the structural unit represented by the formula (4) is a structural unit represented by the formula (5):

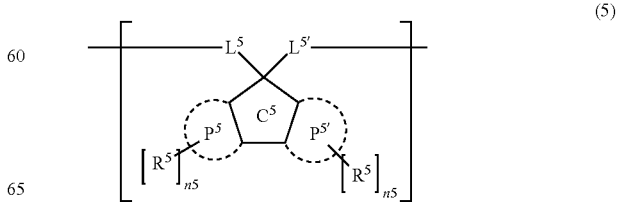

(5)

wherein,

P⁵ and P⁵' are each independently a $C_{6-10}$ aromatic hydrocarbon ring and each of said P⁵ and P⁵' contains two adjacent carbon atoms in $C^5$ as constitution atoms, $R^5$ is each independently $C_{1-6}$ alkyl, halogen, or cyano, n5 is each independently 0, 1, 2, 3, or 4, $L^5$ is each independently a single bond or $C_{1-9}$ alkylene, and $L^{5'}$ is each independently a single bond, $C_{1-9}$ alkylene, or hydrogen.

P⁵ and P⁵' are preferably a benzene ring or a naphthalene ring, more preferably a benzene ring.

n5 is preferably 0.

$L^5$ is preferably a single bond or methylene, more preferably a single bond.

$L^{5'}$ is preferably a single bond, methylene or hydrogen, more preferably a single bond or hydrogen.

When the structural unit of formula (5) is positioned at the end of the molecule, an embodiment in which $L^{5'}$ is hydrogen is preferable.

For example, the following structure is a structural unit represented by the formula (5), wherein P⁵ is a benzene ring, P⁵' is a naphthalene ring, n5 are both 0, and $L^5$ and $L^{5'}$ are single bonds.

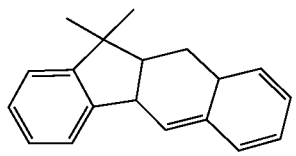

For example, the following allyloxy derivative is composed of one structural unit of the formula (2) and one structural unit of the formula (4). In the formula (2), $Ar^{2a}$ is 9,9-diphenylfluorene and n2 is 2. The group X is bonded to phenyl in diphenylfluorene. In the formula (4), $Ar^{4a}$ and $Ar^{4b}$ are benzene rings and n4 is 0. One Y is a substituted methylene group bonding to the other portion (diphenylfluorene in the formula (2)) of the allyloxy derivative, which is bonded to a portion other than the group X (diphenylfluorene) in the structural unit of the formula (2) of the present allyloxy derivative. The one other Y is a single bond. Here, the structural unit of the formula (4) can also be represented by the formula (5), wherein $L^5$ is a single bond which is bonded to a portion other than the group X (diphenylfluorene) in the structural unit of the formula (2) of the present allyloxy derivative.

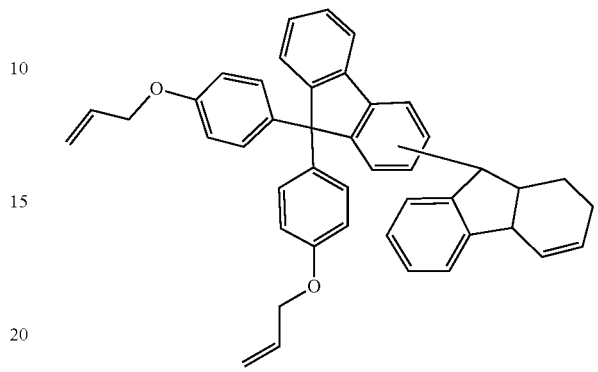

For example, the following allyloxy derivative is composed of two structural units of the formula (2) and two structural units of the formula (4). The structural units of the formula (2) are the same as described above. In the structural units of the formula (4), $Ar^{4a}$ and $Ar^{4b}$ are benzene rings and n4 is 0. One Y is a substituted methylene group bonding to the other portion (diphenylfluorene in the formula (2)) of the allyloxy derivative, which is bonded to a portion other than the group X (diphenylfluorene) in the structural unit of the formula (2) of the present allyloxy derivative. The one other Y is a single bond.

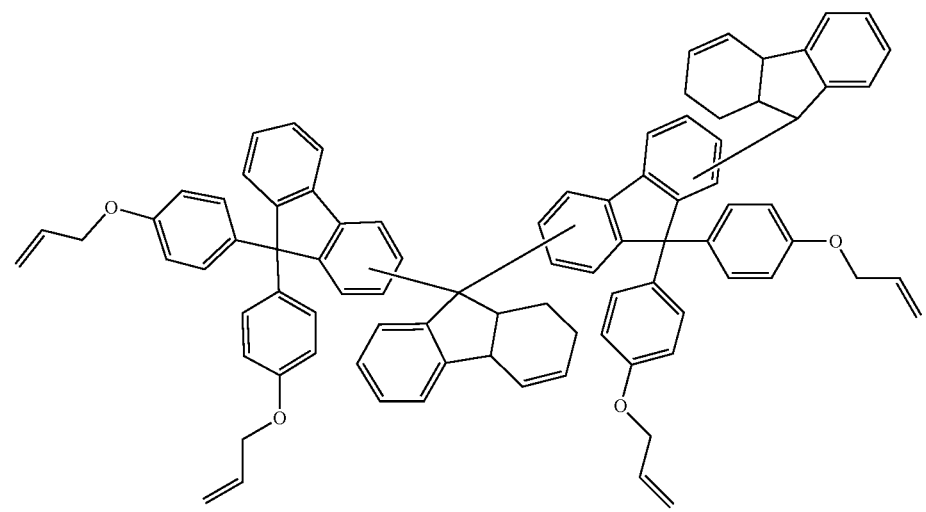

For example, the following allyloxy derivative is composed of two structural units of the formula (2) and two structural units of the formula (4). The structural units of the formula (2) are the same as described above. In the structural units of the formula (4), $Ar^{4a}$ and $Ar^{4b}$ are benzene rings and n4 is 0. One Y is a substituted methylene group, which is bonded to the other portion (diphenylfluorene in the formula (2)) of the allyloxy derivative and the structural unit of the other formula (4). The one other Y is a single bond.

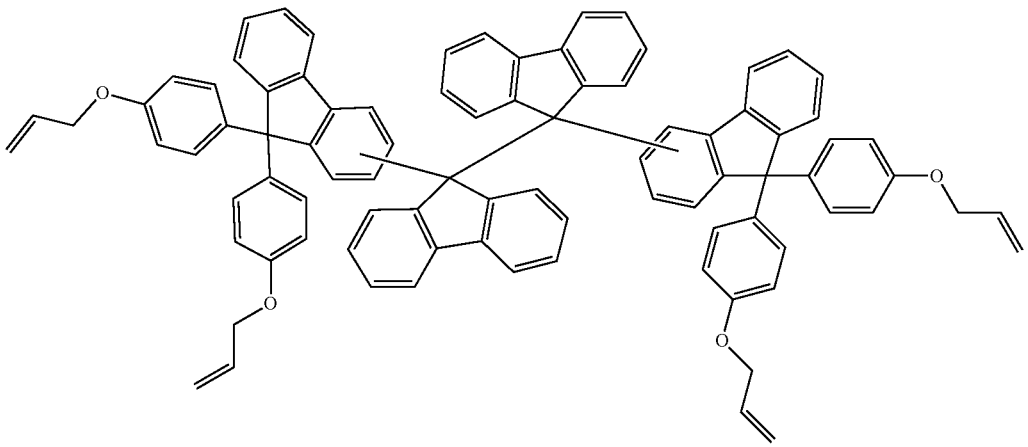

One of the preferred examples of the allyloxy derivative of the present invention is a compound comprising the following structure.

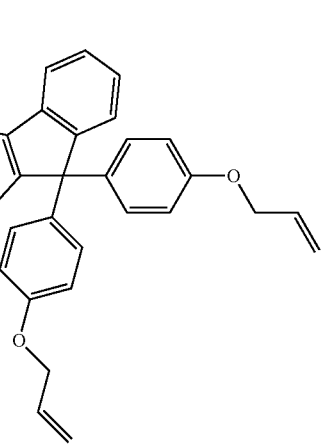

wherein, n is an integer representing the number of repetitions. When the allyloxy derivative of the present invention is a polymer (here, including a dimer), one preferable embodiment is that the polymer is an alternating copolymer.

The structural unit represented by the formula (2) is preferably 30-95 mol %, more preferably 40-70 mol %, further preferably 40-60 mol %, based on the all structural units of said allyloxy derivative. Similarly, the ratio of the structural unit represented by the formula (4) is preferably 10-70 mol %, more preferably 30-60 mol %, further preferably 40-60 mol %, based on the all structural units of said allyloxy derivative.

The present invention provides an electronic material comprising said allyloxy derivative, preferably consisting only of said allyloxy derivative. Said electronic material means a material to be used in the manufacture of electronic components and does not need to finally remain as a constituent element of the electronic component. Further, the present invention provides a semiconductor material comprising said allyloxy derivative, preferably comprising only of said allyloxy derivative. Said semiconductor material means a material to be used for manufacturing a semiconductor device and does not need to finally remain as a constituent element of the semiconductor device.

In the resist underlayer forming composition according to the present invention, it is preferable that the solid content contained therein has a high carbon content. That is, when one or more solid components contained in the composition satisfy the following formula (6), the carbon content is high, which is preferable. For example, when the present resist underlayer forming composition comprises two kinds consisting of the allyloxy derivative and a surfactant as solid components, it is preferable that the solid components as a whole satisfy the following formula (6), and can be calculated using molar ratios.

$$1.5 \leq \{\text{total number of atoms}/(\text{number of C} - \text{number of O})\} \leq 3.5 \quad (6)$$

where, the total number of atoms is the number of atoms of all the monomer molecules when the solid component is a monomer or the number of atoms of one repeating unit when the solid component is a polymer, the number of C is the number of carbon atoms in the total number of atoms, and the number of O is the number of oxygen atoms in the total number of atoms.

Preferably, the formula (6) is the formula (6)' or the formula (6)".

$$1.5 \leq \{\text{total number of atoms}/(\text{number of C} - \text{number of O})\} \leq 2.4 \quad (6)'$$

$$1.8 \leq \{\text{total number of atoms}/(\text{number of C} - \text{number of O})\} \leq 2.4 \quad (6)''$$

The method of synthesizing the allyloxy derivative according to the present invention is not particularly limited, but it can be manufactured, according to a known method, by reacting a structure comprising a hydroxyl group with a vinyl derivative.

The allyloxy derivative of the present invention can be synthesized by the following method.

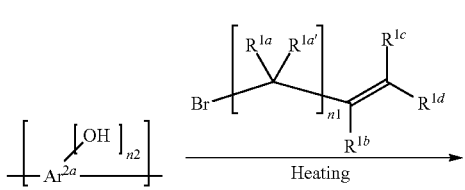

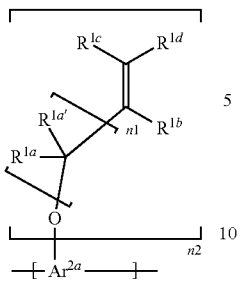

In addition, specific embodiments of the method of synthesizing specific structures are described in the synthesis examples described later and can be combined with the usual method.

The content of the allyloxy derivative according to the present invention is preferably 2-60 mass %, more preferably 2-40 mass %, further preferably 2-10 mass %, still more preferably 3-5 mass %, based on the total mass of the composition according to the present invention. Obviously, when the allyloxy derivative according to the present invention is a combination of plural kinds, the content of the allyloxy derivative according to the present invention is obtained from the sum of plural allyloxy derivatives.

In the composition according to the present invention, the allyloxy derivative according to the present invention is suitable for forming an underlayer from the ease of cross-linking, and more suitable for the process of photo-cross-linking (photocuring) since it can be self-cross-linked by accepting light.

[Solvent]

Examples of the solvent to be used in the composition according to the present invention include water, a hydrocarbon solvent, an ether solvent, an ester solvent, an alcohol solvent, a ketone solvent, or any mixture of any of these.

Specific examples of the solvent include water, n-pentane, i-pentane, n-hexane, i-hexane, n-heptane, i-heptane, 2,2,4-trimethylpentane, n-octane, i-octane, cyclohexane, methylcyclohexane, benzene, toluene, xylene, ethylbenzene, trimethylbenzene, methylethylbenzene, n-propylbenzene, i-propylbenzene, diethylbenzene, i-butylbenzene, triethylbenzene, di-i-propylbenzene, n-amyl naphthalene, trimethyl benzene, methanol, ethanol, n-propanol, i-propanol, n-butanol, i-butanol, sec-butanol, t-butanol, n-pentanol, i-pentanol, 2-methylbutanol, sec-pentanol, t-pentanol, 3-methoxybutanol, n-hexanol, 2-methylpentanol, sec-hexanol, 2-ethylbutanol, sec-heptanol, heptanol-3, n-octanol, 2-ethylhexanol, sec-octanol, n-nonyl alcohol, 2,6-dimethylheptanol-4, n-decanol, sec-undecyl alcohol, trimethyl nonyl alcohol, sec-tetradecyl alcohol, sec-heptadecyl alcohol, phenol, cyclohexanol, methylcyclohexanol, 3,3,5-trimethylcyclohexanol, benzyl alcohol, phenylmethyl carbinol, diacetone alcohol, cresol, ethylene glycol, propylene glycol, 1,3-butylene glycol, pentanediol-2,4,2-methylpentanediol-2,4, hexanediol-2,5, heptanediol-2,4,2-ethylhexanediol-1,3, diethylene glycol, dipropylene glycol, triethylene glycol, tripropylene glycol, glycerin, acetone, methyl ethyl ketone, methyl n-propyl ketone, methyl n-butyl ketone, diethyl ketone, methyl i-butyl ketone, methyl n-pentyl ketone, ethyl n-butyl ketone, methyl n-hexyl ketone, di-i-butyl ketone, trimethylnonane, cyclohexanone, cyclopentanone, methylcyclohexanone, 2,4-pentanedione, acetonylacetone, diacetone alcohol, acetophenone, fenthion, ethyl ether, i-propyl ether, n-butyl ether, n-hexyl ether, 2-ethylhexyl ether, ethylene oxide, 1,2-propylene oxide, dioxolane, 4-methyl dioxolane, dioxane, dimethyl dioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethyl butyl ether, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxytriglycol, tetraethylene glycol di-n-butyl ether, propylene glycol monomethyl ether (PGME), propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, 2-methyltetrahydrofuran; ester solvents such as diethyl carbonate, methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methyl cyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, i-amyl propionate, diethyl oxalate, di-n-butyl oxalate, methyl lactate, ethyl lactate (EL), γ-butyrolactone, n-butyl lactate, n-amyl lactate, diethyl malonate, dimethyl phthalate, diethyl phthalate, propylene glycol 1-monomethyl ether 2-acetate (PGMEA), propylene glycol monoethyl ether acetate and propylene glycol monopropyl ether acetate; N-methylformamide, N,N-dimethylformamide, N,N-diethylformamide, acetamide, N-methylacetamide, N,N-dimethylacetamide, N-methylpropionamide, N-methyl pyrrolidone, dimethyl sulfide, diethyl sulfide, thiophene, tetrahydrothiophene, dimethyl sulfoxide, sulfolane, and 1,3-propane sultone. These solvents can be used alone or in combination of two or more.

[High-Carbon Material]

The composition according to the present invention may further comprise a high-carbon material. By adding the high-carbon material, the composition as a whole can satisfy the above formula (6) (preferably the formula (6)', more preferably the formula (6)"). The high-carbon material in the present specification is a compound different from the allyloxy derivative of the present invention. The high-carbon material may be low molecular weight or high molecular weight material. The high-carbon material is preferably composed only of carbon (C), oxygen (O) and hydrogen (H), and more preferably composed only of carbon (C) and hydrogen (H).

By containing the further high-carbon material in the composition according to the present invention, a resist underlayer better in etching resistance can be obtained. In the formation of the resist underlayer, the embodiment that the high-carbon material is present in the state of not being polymerized in the composition at the time before being cured by ultraviolet irradiation or ultraviolet irradiation after heating is preferable.

The high-carbon material is preferably represented by any one of the following formulas (7), (8), and (9).

These compounds satisfy the above formula (6), preferably further satisfy the formula (6)' or the formula (6)". Each is described later.

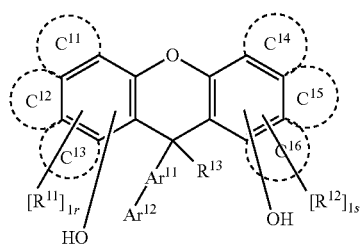
(7)

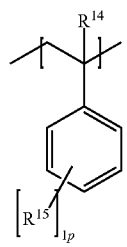
(8)

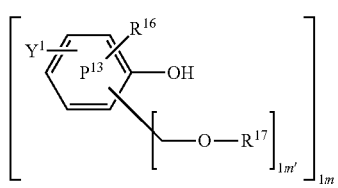
(9)

The high-carbon material represented by the formula (7) is as shown below.

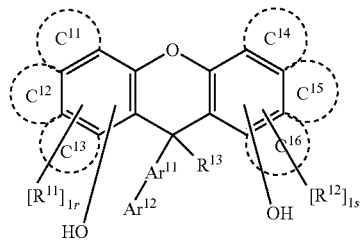
(7)

$Ar^{11}$ is a direct bond, $C_{1-6}$ alkyl, $C_{6-12}$ cycloalkyl, or $C_{6-14}$ aryl. $Ar^{11}$ is preferably a direct bond, $C_{1-6}$ alkyl, or phenyl, more preferably a direct bond, linear $C_3$ alkyl, linear $C_6$ alkyl, tertiary butyl, or phenyl, and further preferably a direct bond or phenyl.

$Ar^{12}$ is $C_{1-6}$ alkyl, $C_{6-12}$ cycloalkyl, or $C_{6-14}$ aryl. $Ar^{12}$ is preferably isopropyl, tertiary butyl, $C_6$ cycloalkyl, phenyl, naphthyl, phenanthryl, or biphenyl, and further preferably phenyl.

$R^{11}$ and $R^{12}$ are each independently $C_{1-6}$ alkyl, hydroxy, halogen, or cyano. $R^{11}$ and $R^{12}$ are preferably each independently methyl, ethyl, propyl, isopropyl, tertiary butyl, hydroxy, fluorine, chlorine, or cyano, and further preferably methyl, hydroxy, fluorine, or chlorine.

$R^{13}$ is hydrogen, $C_{1-6}$ alkyl, or $C_{6-14}$ aryl. $R^{13}$ is preferably hydrogen, $C_{1-6}$ alkyl, or phenyl, more preferably hydrogen, methyl, ethyl, linear $C_5$ alkyl, tertiary butyl, or phenyl, further more preferably hydrogen or phenyl, and still further preferably hydrogen.

When $Ar^{12}$ is $C_{1-6}$ alkyl or $C_{6-14}$ aryl and $R^{13}$ is $C_{1-6}$ alkyl or $C_{6-14}$ aryl, $Ar^{12}$ and $R^{13}$ may be optionally bonded each other to form a hydrocarbon ring.

$1r$ and $1s$ are each independently 0, 1, 2, 3, 4, or 5. $1r$ and $1s$ are preferably each independently 0 or 1, and $1r$ and $1s$ are more preferably each independently 0.

At least one of the $C^{11}$, $C^{12}$ and $C^{13}$ rings each surrounded by the broken line is an aromatic hydrocarbon ring fused with the adjacent aromatic hydrocarbon ring $P^{11}$, and the number of carbon atoms of the aromatic hydrocarbon ring, including carbon atoms of the aromatic hydrocarbon ring $P^{11}$, is preferably $C_{10-14}$ and more preferably $C_{10}$.

At least one of the $C^{14}$, $C^{15}$ and $C^{16}$ rings each surrounded by the broken line is an aromatic hydrocarbon ring fused with the adjacent aromatic hydrocarbon ring $P^{12}$, and the number of carbon atoms of the aromatic hydrocarbon ring, including carbon atoms of the aromatic hydrocarbon ring $P^{12}$, is preferably $C_{10-14}$ and more preferably $C_{10}$.

In the formula (7), the bonding positions of $R^{11}$, $R^{12}$ and OH are not limited.

For example, the compound shown below can have the following structure in the formula (7). The aromatic hydrocarbon ring $P^{11}$ and the aromatic hydrocarbon ring $C^{13}$ are fused each other to form a naphthyl ring, and OH is bonded to the aromatic hydrocarbon ring $C^{13}$. Further, $Ar^{11}$ is a direct bond, $Ar^{12}$ and $R^{13}$ are phenyl, and $Ar^{12}$ and $R^{13}$ are bonded each other to form a hydrocarbon ring (fluorene).

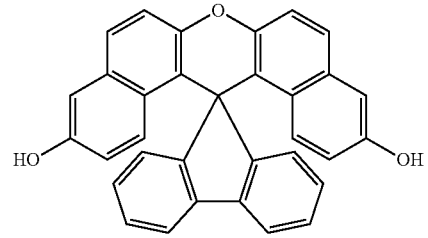 [SMILES: Oc1ccc2c3c(ccc2c1)Oc1ccc2cc(O)ccc2c1C31c2ccccc2-c2ccccc21]

In particular, the high-carbon material represented by the formula (7) is denoted by the following formula.

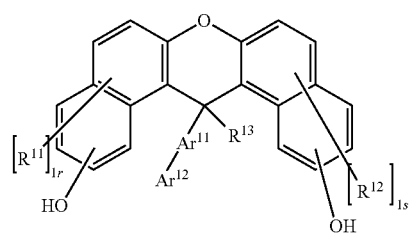
(7)-1

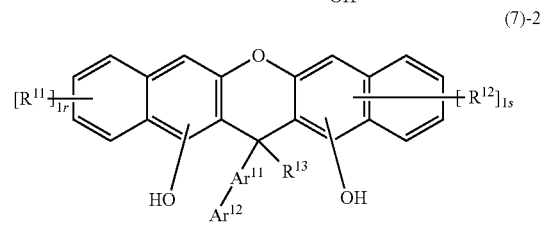
(7)-2

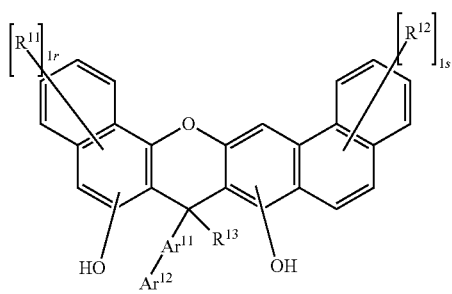

(7)-3

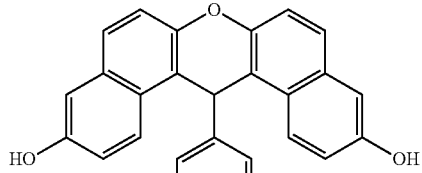

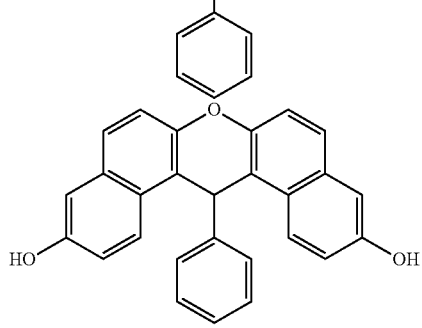

In the formulas (7)-1, (7)-2, and (7)-3, the definitions of $Ar^{11}$, $Ar^{12}$, $R^{11}$, $R^{12}$, $R^{13}$, 1r and 1s are the same as described above. Further, preferred examples of these are each independently the same as described above. Among the high-carbon materials of the formula (7), the high-carbon material represented by the formula (7)-1 is more preferable.

The present carbon-containing underlayer can contain one or more high-carbon materials represented by the formula (7). Sole use of the high-carbon material is preferred. For example, the following two compounds may be comprised together in the composition according to the invention as the high-carbon material.

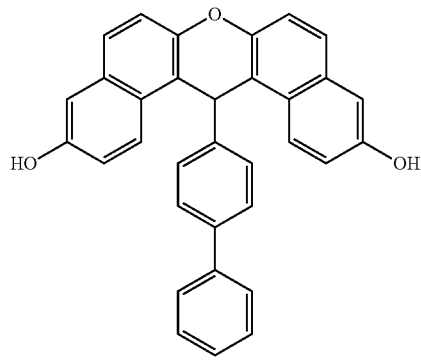

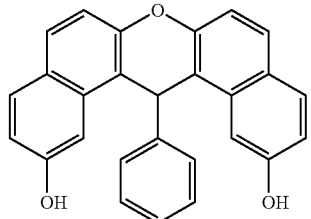

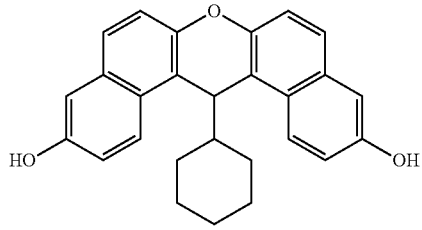

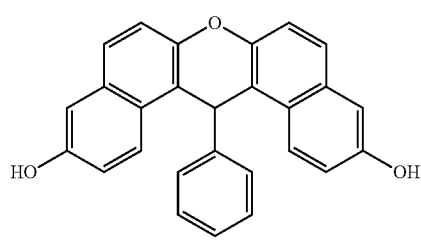

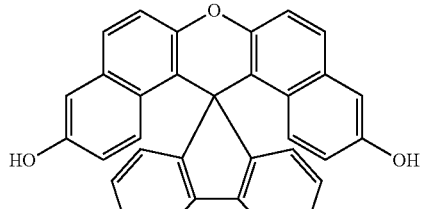

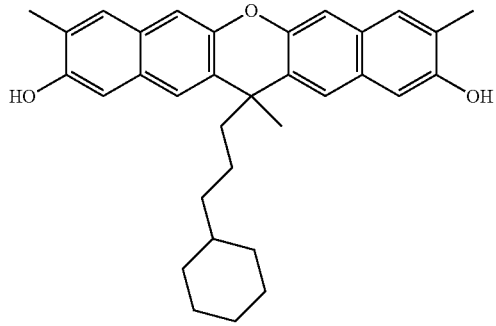

For the sake of explanation, specific examples of the high-carbon material represented by the formula (7) are shown below, but these are not intended to limit the present invention.

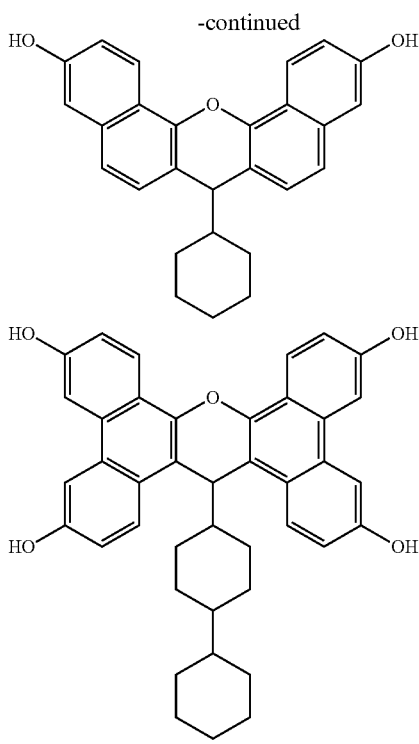

The high-carbon material represented by the formula (8) is the following polymer.

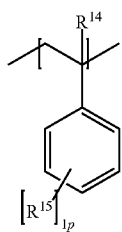

$R^{14}$ is hydrogen, $C_{1-6}$ alkyl, halogen, or cyano. $R^{14}$ is preferably hydrogen, methyl, ethyl, propyl, isopropyl, tertiary butyl, fluorine, chlorine, or cyano, more preferably hydrogen, methyl, fluorine, or chlorine, and particularly preferably hydrogen.

$R^{15}$ is $C_{1-6}$ alkyl, halogen, or cyano. $R^{15}$ is preferably methyl, ethyl, propyl, isopropyl, tertiary butyl, fluorine, chlorine, or cyano, and more preferably methyl, fluorine, or chlorine.

p is 0, 1, 2, 3, 4, or 5, preferably 0 or 1, and particularly preferably 0.

In the high-carbon material represented by formula (8), each $R^{14}$ and $R^{15}$ may be independently identical to or different from each other, and from the viewpoint of reduction of the production cost, it is preferable that $R^{14}$ and/or $R^{15}$ is identical.

In the present invention, the weight-average molecular weight can be measured by gel permeation chromatography (GPC). In this measurement, one suitable example is to use a GPC column at 40 degrees Celsius, elution solvent tetrahydrofuran at 0.6 mL/min and monodisperse polystyrene as a standard.

The weight-average molecular weight (Mw) of the high-carbon material represented by the formula (8) is preferably 5,000-50,000, and further preferably 8,000-40,000.

The high-carbon material represented by the formula (9) is shown below.

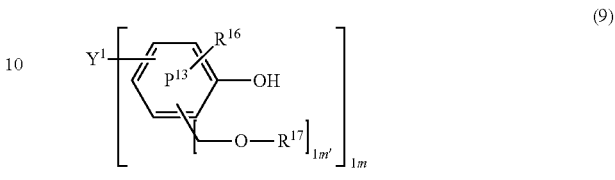

The ring $P^{13}$ is phenyl comprising hydroxyl.

$Y^1$ is $C_{1-6}$ alkyl, $C_{6-14}$ aryl, $C_{6-12}$ cycloalkyl, $C_{7-20}$ aralkyl, $C_{7-20}$ alkyl-substituted aralkyl, $C_{7-20}$ cycloalkyl-substituted alkylcycloalkyl, or a direct bond connecting the two rings $P^{13}$ to each other. In an embodiment, $Y^1$ is preferably methyl, branched or linear $C_{2-4}$ alkyl, phenyl, naphthyl, anthracene, $C_{12}$ cycloalkyl, $C_{15}$ aralkyl, or a direct bond connecting the two rings $P^{13}$ to each other, more preferably methyl, branched $C_{2-3}$ alkyl, phenyl, naphthyl, anthracene, $C_{12}$ cycloalkyl, anthracenylmethyl, or a direct bond connecting the two rings $P^{13}$ to each other, and further preferably methyl. In another embodiment, $Y^1$ is preferably methyl, branched or linear $C_{2-4}$ alkyl, phenyl, naphthyl, anthracene, fluorene, $C_6$ cycloalkyl, $C_{12}$ cycloalkyl, $C_{15}$ aralkyl, $C_{11}$ alkyl-substituted aralkyl, or $C_{15}$ cycloalkyl-substituted alkylcycloalkyl, more preferably methyl, branched $C_{2-3}$ alkyl, phenyl, naphthyl, anthracene, $C_{12}$ cycloalkyl(cyclododecane), anthracenylmethyl, $C_{11}$ alkyl-substituted aralkyl, or $C_{15}$ cycloalkyl-substituted alkylcycloalkyl, and further preferably methyl or cyclododecane.

$R^{16}$ is hydrogen, methyl, ethyl, phenyl, methylol (—$CH_2OH$), $C_{1-3}$ alkoxymethyl, or $C_{6-12}$ cycloalkyl. In an embodiment, $R^{16}$ is preferably methyl, phenyl, methylol, or methoxymethyl ($C_1$ alkoxymethyl), more preferably methylol or methoxymethyl, and further preferably methylol. In another embodiment, $R^{16}$ is preferably hydrogen, methyl, phenyl, methylol, methoxymethyl ($C_1$ alkoxymethyl), or $C_6$ cycloalkyl, and more preferably methylol, methoxymethyl, or $C_6$ cycloalkyl.

$R^{17}$ is hydrogen or $C_{1-3}$ alkyl. $R^{17}$ is preferably hydrogen or methyl, and more preferably hydrogen.

1m is 1, 2, 3, or 4. When 1m is 2, 3, or 4, $Y^1$ connects, as a linker, the bracketed groups to each other. 1m is preferably 1 or 2, and more preferably 1.

1m' is 0 or 1, and preferably 1.

The embodiment in which $Y^1$ or $R^{16}$ (except when $R^{16}$ is hydrogen) is bonded at the ortho position relative to the hydroxyl group directly bonded to the benzene ring in the formula (9) is preferable, and the embodiment in which $R^{16}$ is bonded at an ortho position is further preferable. The embodiment in which $Y^1$ or $R^{16}$ (except when $R^{16}$ is hydrogen) is bonded at a para position relative to the hydroxyl group directly bonded to the benzene ring in the formula (9) is preferable, and the embodiment in which $Y^1$ is bonded at the para position is further preferable.

For example, in the compound shown at the lower left, $Y^1$ is methyl, $R^{16}$ is methyl, $R^{17}$ is hydrogen, 1m is 2, and 1m' is 1. $Y^1$ is bonded at an ortho position relative to the hydroxyl group directly bonded to the benzene ring in the formula (9), and connects, as a methylene linker, the two rings $P^{13}$ to each other. $R^{16}$ is bonded at a para position relative to the hydroxyl group directly bonded to the benzene ring.

For example, in the compound shown at the lower right, $Y^1$ is a direct bond connecting the two $P^{13}$ rings to each other, $R^{16}$ is methoxymethyl, $R^{17}$ is methyl, 1m is 2, and m' is 1.

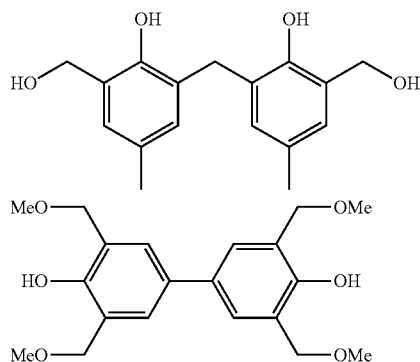

For the illustrative purpose, specific examples of the high-carbon material represented by the formula (9) are shown below, but these are not intended to limit the present invention.

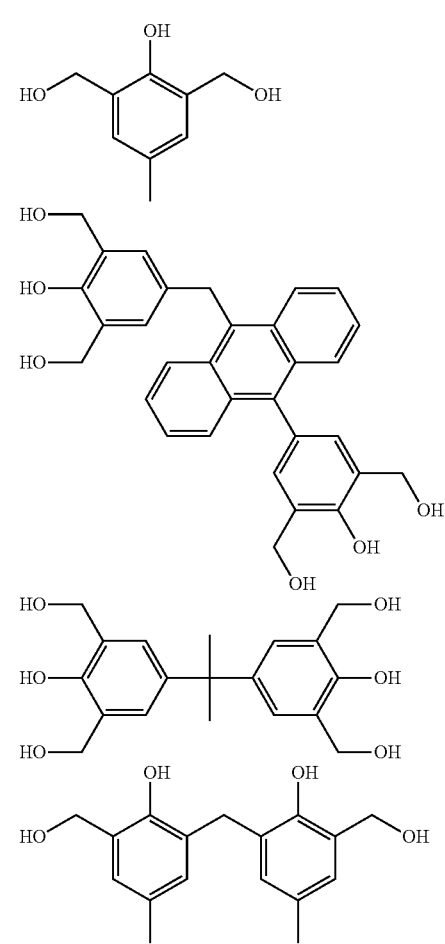

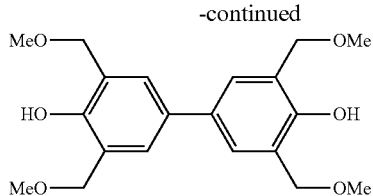

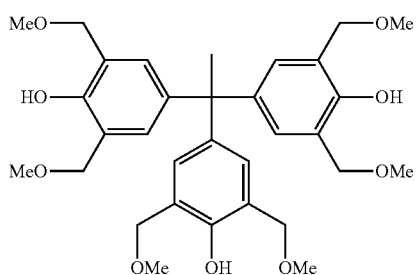

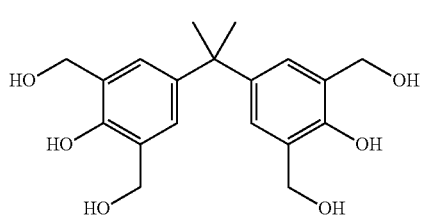

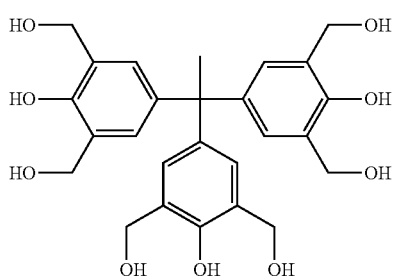

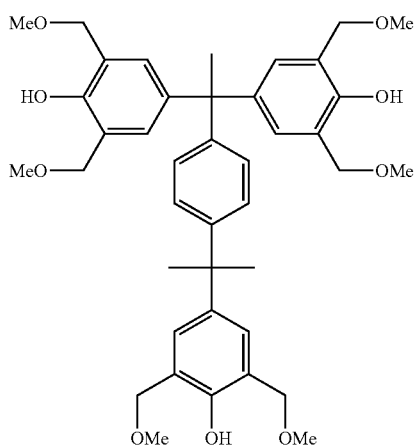

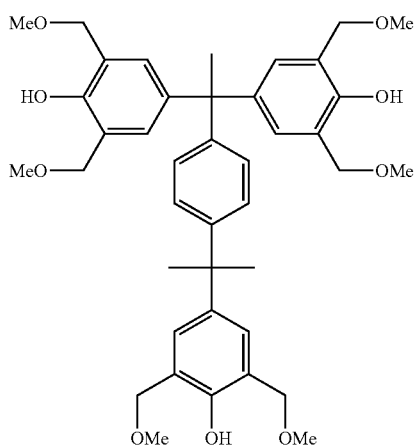

-continued
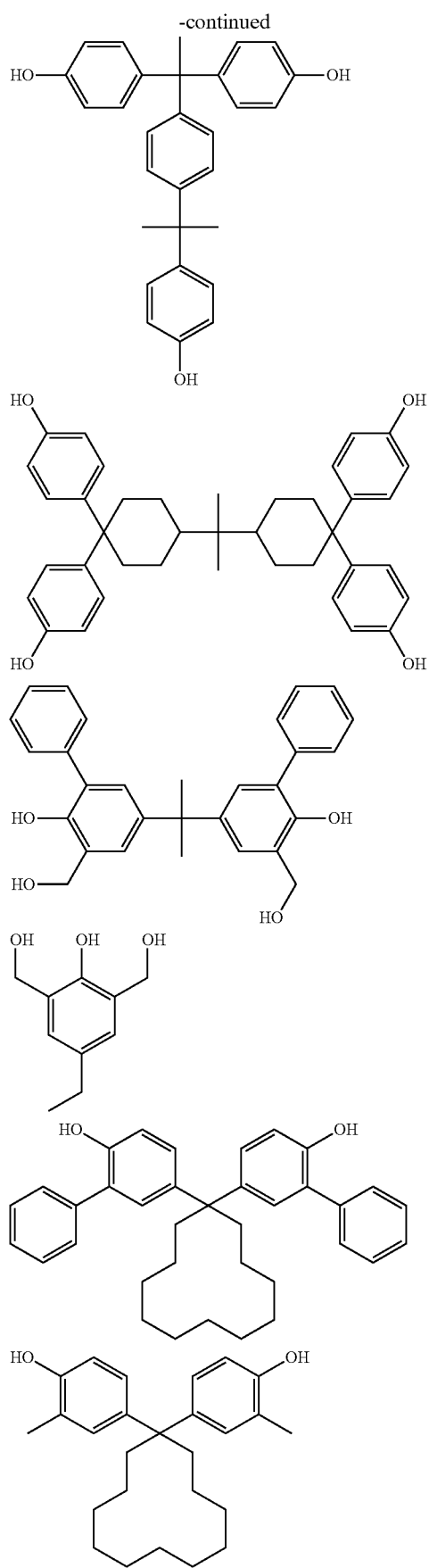
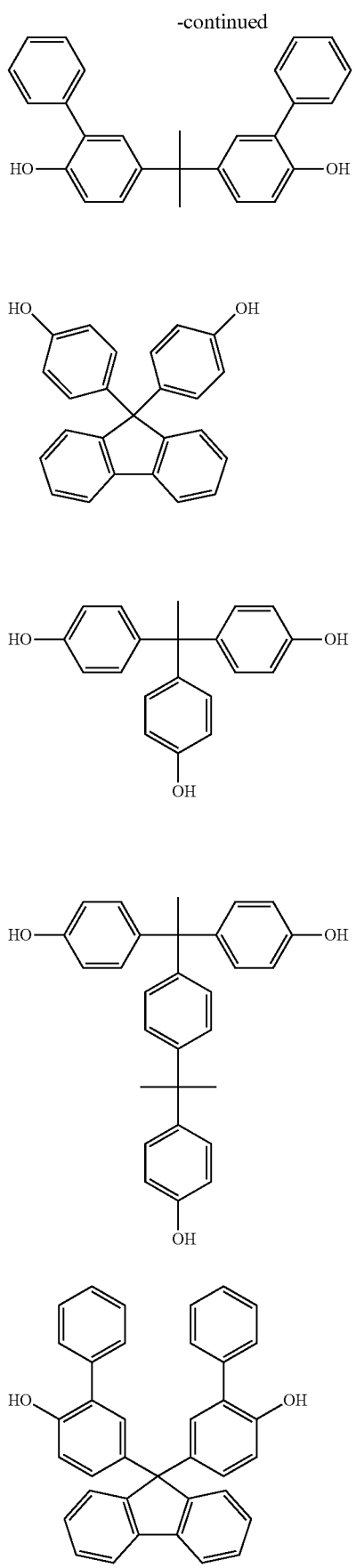

-continued

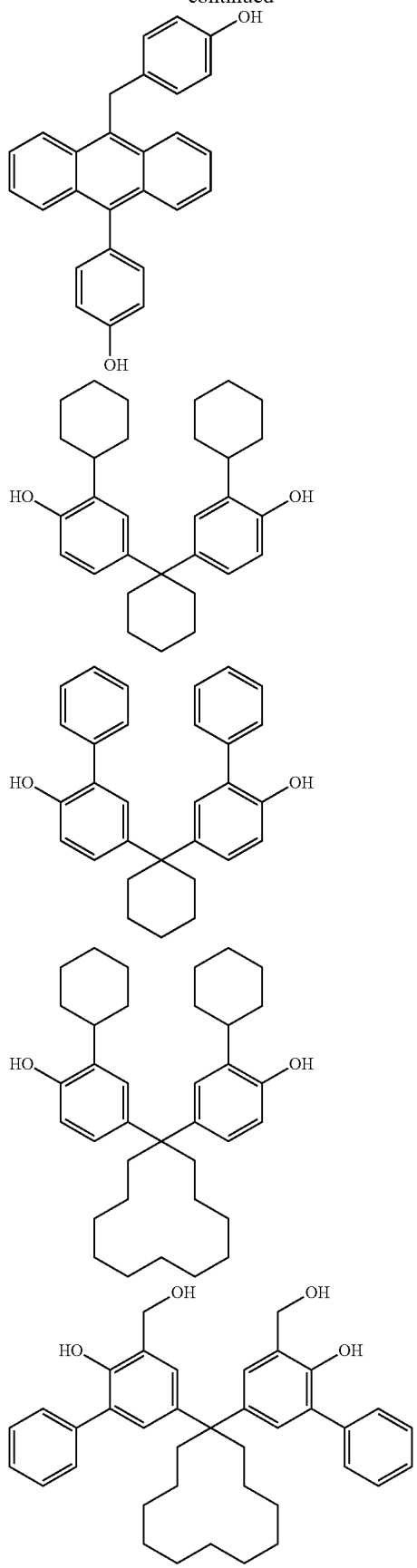

-continued

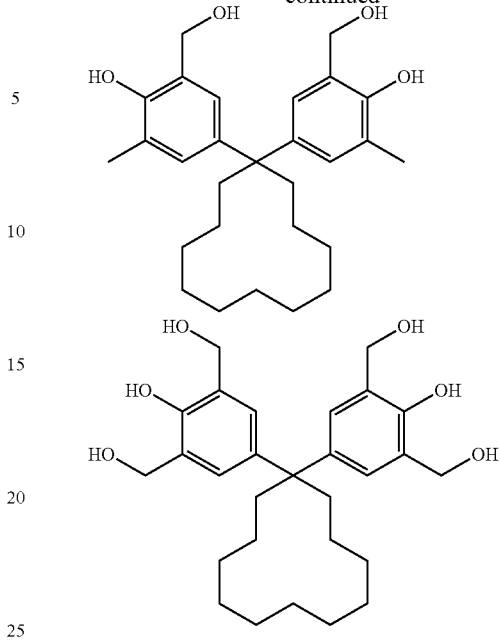

The high-carbon material is represented by any one of the formulas (7), (8), and (9), and the present carbon-containing underlayer forming composition may contain one or more of these. Preferably, the composition according to the present invention comprises solely one high-carbon material represented by any one of the formulas (7), (8), and (9).

In the present invention, the amount of the high-carbon material is preferably 5-120%, and more preferably 7-100%, relative to the mass of the allyloxy derivative according to the present invention. When the amount of the high-carbon material is increased, for example, to 50-120% relative to the mass of the allyloxy derivative according to the present invention, the etching resistance can be increased.

The composition according to the present invention may further comprise a surfactant, a cross-linking agent, an acid generator, a radical generator, a photopolymerization initiator, an agent for enhancing the adhesion to substrates, or any mixture of any of these.

[Surfactant]

The surfactant is useful for suppressing the generation of pinholes and strains and improving coatability and solubility. The content of the surfactant relative to the composition according to the present invention is preferably 0-5 mass %, and more preferably 0.1-3 mass %. It is also a preferred embodiment of the present invention that no surfactant is contained in the present composition (0 mass %).

Examples of the surfactant include polyoxyethylene alkyl ether compounds such as polyoxyethylene lauryl ether, polyoxyethylene stearyl ether and polyoxyethylene oleyl ether; polyoxyethylene alkylaryl ether compounds such as polyoxyethylene octylphenol ether and polyoxyethylene nonylphenol ether; polyoxyethylene-polyoxypropylene block copolymer compounds; sorbitan fatty acid ester compounds such as sorbitan monolaurate, sorbitan monopalmitate, sorbitan monostearate, sorbitan trioleate and sorbitan tristearate; and polyoxyethylene sorbitan fatty acid ester compounds such as polyoxyethylene sorbitan monolaurate, polyoxyethylene sorbitan monopalmitate, polyoxyethylene sorbitan monostearate and polyoxyethylene sorbitan tristearate. Further, fluorine-based surfactants such as EFTOP EF301, EF303 and EF352 (trade name, manufactured by Tohkem Products Corp.), MEGAFAC F171, F173, R-08, R-30 and R-2011 (trade name, manufactured by DIC Corporation), FLUORAD FC430 and FC431 (manufactured by Sumitomo 3M Limited), ASAHI GUARD AG710 and SURFLON S-382, SC101, SC102, SC103, SC104, SC105 and SC106 (trade name, manufactured by Asahi Glass Co., Ltd.); and organosiloxane polymer KP341 (manufactured by Shin-Etsu Chemical Co., Ltd.), and the like can be referred.

[Cross-Linking Agent]

The cross-linking agent is useful to increase the film formability when forming the resist underlayer according to the present invention, to prevent the resist underlayer from being intermixed with the upper layer film (such as a silicon-containing interlayer and a resist), and to eliminate diffusion of low molecular weight components into the upper layer. The content of the cross-linking agent is preferably 0-300,000 ppm relative to the composition according to the present invention. In the case where a cross-linking agent is contained, said content is preferably 0.1-100,000 ppm, more preferably 1-50,000 ppm, and further preferably 10-10,000 ppm. The composition according to the present invention can exhibit the effects of the present invention even if the cross-linking agent is not contained in an effective amount. In this case, the content of the cross-linking agent relative to the present composition is preferably 0-20,000 ppm, more preferably 0-5,000 ppm, further preferably 0-1,000 ppm, and even more preferably 0-100 ppm. It is also a preferred embodiment of the present invention to make no cross-linking agent be contained (0 ppm) in the present composition.

As the cross-linking agent, melamine compounds, guanamine compounds, glycoluril compounds or urea compounds substituted by at least one group selected from a methylol group, an alkoxymethyl group, and an acyloxymethyl group; epoxy compounds; thioepoxy compounds; isocyanate compounds; azide compounds; and compounds comprising a double bond such as an alkenyl ether group can be referred. These may be used as an additive or may be introduced as a pendant group into a polymer side chain. Further, compounds comprising a hydroxy group can also be used as a cross-linking agent.

Examples of the epoxy compounds mentioned above include tris(2,3-epoxypropyl)isocyanurate, trimethylolmethane triglycidyl ether, trimethylolpropane triglycidyl ether, and triethylolethane triglycidyl ether. Specific examples of the melamine compounds include hexamethylolmelamine, hexamethoxymethylmelamine, compounds derived by methoxymethylation of 1-6 methylol groups of hexamethylolmelamine and mixtures of such compounds, hexamethoxyethylmelamine, hexaacyloxymethylmelamine, compounds derived by acyloxymethylation of 1-6 methylol groups of hexamethylolmelamine or mixtures of such compounds. As the guanamine compounds, tetramethylolguanamine, tetramethoxymethylguanamine, compounds derived by methoxymethylation of 1-4 methylol groups of tetramethylolguanamine and mixtures of such compounds, tetramethoxyethylguanamine, tetraacyloxyguanamine, compounds derived by acyloxymethylation of 1-4 methylol groups of tetramethylolguanamine and mixtures of such compounds can be referred. As the glycoluril compounds, tetramethylolglycoluril, tetramethoxyglycoluril, tetramethoxymethylglycoluril, compounds derived by methoxymethylation of 1-4 methylol groups of tetramethylolglycoluril or mixtures of such compounds, compounds derived by acyloxymethylation of 1-4 methylol groups of tetramethylolglycoluril or mixtures of such compounds can be referred. As the urea compounds, tetramethylolurea, tetramethoxymethylurea, compounds derived by methoxymethylation of 1-4 of methylol groups of tetramethylolurea or mixtures of such compounds, and tetramethoxyethylurea, and the like can be referred.

As the compounds containing an alkenyl ether group, ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, trimethylolpropane trivinyl ether, and the like can be referred.

As the other cross-linking agents, those represented by the following formulas can be referred.

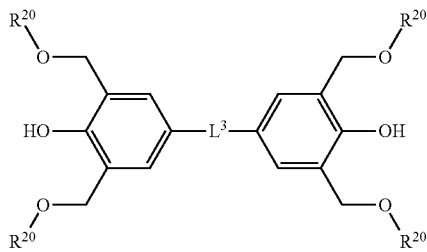

wherein, $L^3$ is a direct bond, substituted or unsubstituted $C_{1-3}$ alkyl, and $R^{20}$ is hydrogen or methyl. $L^3$ is preferably a direct bond or methyl, more preferably a direct bond. The substituent of $C_{1-3}$ alkyl is preferably hydrogen, methyl, $C_{6-10}$ aryl, or any one of the following two formulas, more preferably methyl or any one of the following two formulas.

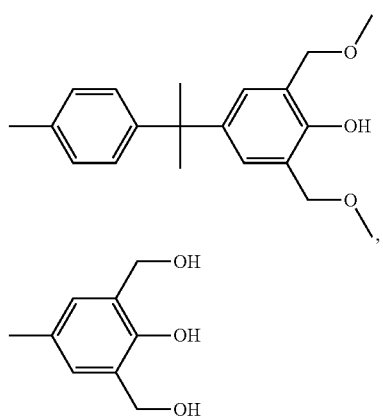

Specific examples of the cross-linking agent represented by the above formulas are as shown below, but the scope of the present invention is not limited thereto.

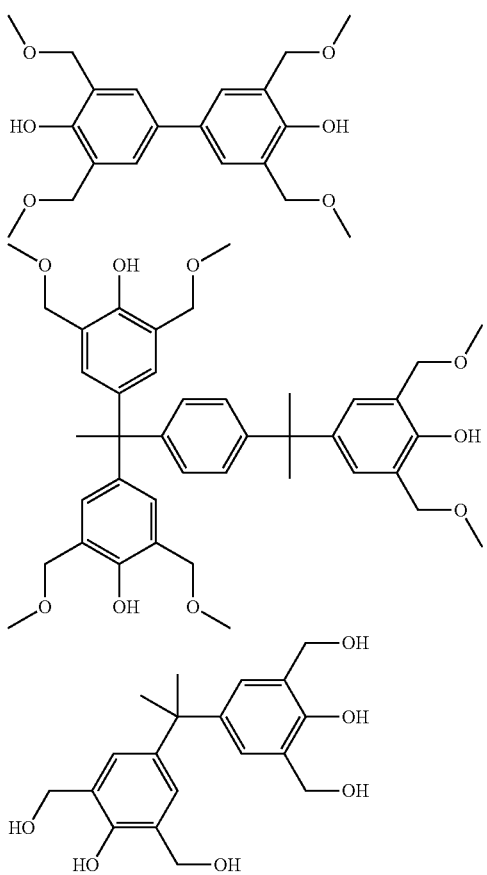

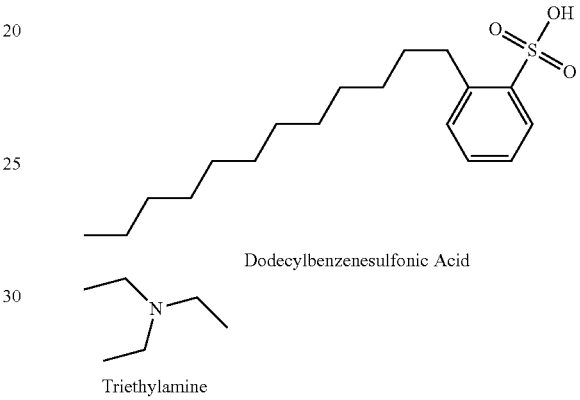

Dodecylbenzenesulfonic Acid

Triethylamine

[Acid Generator]

The acid generator is useful from the viewpoint of improvement of heat resistance (acceleration of cross-linking reaction). The content of the acid generator relative to the composition according to the present invention is preferably 0-50,000 ppm, more preferably 0-1,000 ppm, and further preferably 0-500 ppm. It is also a preferred embodiment of the present invention to make no acid generator be contained (0 ppm) in the present composition.

As the acid generator, a thermal acid generator (TAG) capable of generating a strong acid by heating can be referred. Preferred thermal acid generators are those which are activated at a temperature exceeding 80 degrees. Examples of the thermal acid generator include metal-free sulfonium salts and metal-free iodonium salts, for example, triarylsulfonium, dialkylarylsulfonium and diarylalkylsulfonium salts of strong non-nucleophilic acids, and alkylaryliodonium and diaryliodonium salts of strong non-nucleophilic acids; and ammonium, alkylammonium, dialkylammonium, trialkylammonium, and tetraalkylammonium salts of strong non-nucleophilic acids. Further, covalent thermal acid generators are also considered as useful additives, and examples thereof include 2-nitrobenzyl esters of alkyl or aryl sulfonic acids and other sulfonic acid esters which are thermally decomposed to give free sulfonic acid. Examples thereof include diaryliodonium perfluoroalkyl sulfonates, diaryliodonium tris(fluoroalkylsulfonyl)methides, diaryliodonium bis(fluoroalkylsulfonyl)methides, diaryliodonium bis(fluoroalkylsulfonyl)imides, and diaryliodonium quaternary ammonium perfluoroalkyl sulfonates. Examples of labile esters include 2-nitrobenzyl tosylate, 2,4-dinitrobenzyl tosylate, 2,6-dinitrobenzyl tosylate, and 4-nitrobenzyl tosylate; benzenesulfonates such as 2-trifluoromethyl-6-nitrobenzyl 4-chlorobenzenesulfonate and 2-trifluoromethyl-6-nitrobenzyl 4-nitrobenzenesulfonate; phenolic sulfonate esters such as phenyl 4-methoxybenzenesulfonate; quaternary ammonium tris(fluoroalkylsulfonyl)methides, quaternary alkylammonium bis(fluoroalkylsulfonyl)imides, and alkylammonium salts of organic acids such as triethylammonium salt of 10-camphorsulfonic acid. Various aromatic (anthracene, naphthalene, or benzene derivative) sulfonic acid amine salts, including those disclosed in U.S. Pat. Nos. 3,474,054, 4,200,729, 4,251,665 and 5,187,019, can be used as the TAG.

Specific examples of the acid generator that can be contained in the composition according to the present invention are as shown below, but the scope of the present invention is not limited thereto.

[Radical Generator]

The radical generator can be used to initiate polymerization. The content of the acid generator relative to the composition according to the present invention is preferably 0-50,000 ppm, more preferably 0-1,000 ppm, and further preferably 0-500 ppm. It is also a preferred embodiment of the present invention to make no radical generator be contained (0 ppm) in the present composition.

The radical generator is one which generates radicals by heating, and examples thereof include azo compounds and peroxides. Specific examples of the radical generator include organic peroxides, including hydroperoxides such as diisopropylbenzene hydroperoxide, cumene hydroperoxide and t-butyl hydroperoxide, dialkyl peroxides such as α,α-bis(t-butylperoxy-m-isopropyl)benzene, dicumyl peroxide, 2,5-dimethyl-2,5-bis(t-butylperoxy)hexane, t-butyl cumyl peroxide, di-t-butyl peroxide, 2,5-dimethyl-2,5-bis(t-butylperoxy)hexyne-3 and t-butyl peroxy-2-ethylhexanoate, ketone peroxides, peroxyketals such as n-butyl 4,4-di(t-butylperoxy)valerate, diacyl peroxides, peroxydicarbonates, and peroxyesters; and azo compounds such as 2,2'-azobisisobutyronitrile, 1,1'-(cyclohexane-1-1-carbonitrile), 2,2'-azobis(2-cyclopropylpropionitrile), and 2,2'-azobis(2,4-dimethylvaleronitrile). These thermal radical generators may be used alone or in combination of two or more and are preferably used alone. In the present resist underlayer forming composition, these known radical generators can be used, and these radical generators are available, for example, from NOF Corporation.

[Photopolymerization Initiator]

The photopolymerization initiator is a compound that is modified upon irradiation with light, and thereby polymerizing a solid component of a composition or becoming a trigger for the polymerization. The content of the photopolymerization initiator relative to the composition according to the present invention is preferably 0-50,000 ppm, more preferably 0-1,000 ppm, and further preferably 0-500 ppm. It is also a preferred embodiment of the present invention to make no photopolymerization initiator be contained (0 ppm) in the present composition.

As the photopolymerization initiator, radical type photopolymerization initiators (such as alkylphenone type photopolymerization initiators, acylphosphine oxide type photopolymerization initiators, intramolecular hydrogen abstraction type photopolymerization initiators, oxime ester type photopolymerization initiators and blends of photopolymerization initiators) and cationic photopolymerization initiators are suitable. Radical type photopolymerization initiators that generate radicals upon irradiation with light are suitable for the present composition. As the photopolymerization initiator, known polymerization initiators can be used, and preferred examples thereof include 2-methyl-1-(4-methylthiophenyl)-2-morpholinopropan-1-one, 2,2-dimethoxy-1,2-diphenylethan-1-one, 1-[4-(2-hydroxyethoxy)-phenyl]-2-hydroxy-2-methyl-1-propan-1-one, 1-hydroxy-cyclohexyl-phenyl-ketone, 2-hydroxy-2-methyl-1-phenyl-propan-1-one, iodonium, (4-methylphenyl)[4-(2-methylpropyl)phenyl]-hexafluoro phosphate, a mixture of 2-[2-oxo-2-phenylacetoxyethoxy]ethyl ester and 2-(2-hydroxyethoxy)ethyl ester, phenylglycolate, benzophenone, and the like. Examples of commercially available photopolymerization initiators include "OXE01", "OXE02", "369", "907", "651", "2959", "184", "250" and "754" of "IRGACURE" series; "MBF", "BP" and "1173" of "DAROCUR" series, manufactured by BASF Japan Ltd.; or any mixture of any of these. The photopolymerization initiator is preferably a single one.

The present composition may further combine a photoinitiation auxiliary with the photopolymerization initiator. The content of the photoinitiation auxiliary relative to the composition according to the present invention is preferably 0-50,000 ppm, more preferably 0-1,000 ppm, and further preferably 0-500 ppm. It is also a preferred embodiment of the present invention to make no photoinitiation auxiliary be contained (0 ppm) in the present composition. Examples of the photoinitiation auxiliary include triethanolamine, methyl diethanolamine and the like.

[Other Components]

The composition according to the present invention may further contain other components such as an agent for enhancing the adhesion to substrate, a lubricant, a monomeric dye, a lower alcohol ($C_{1-6}$ alcohol), a surface leveling agent, an anti-foaming agent, an antiseptic agent, and the like. The total content of these components relative to the composition according to the present invention is preferably 0-50,000 ppm, more preferably 0-10,000 ppm, and further preferably 0-500 ppm. It is also one embodiment of the present invention to make no these components be contained (0 ppm) in the present composition.

[Method of Manufacturing Resist Underlayer]

One embodiment of the method of manufacturing a resist underlayer according to the present invention is described. As described above, the resist underlayer in the present invention is a carbon-containing film formed between a substrate and a resist layer, and one preferred embodiment of the present invention is a planarization film. The planarization film forming composition in the present invention is a composition by which a film is formed between a substrate and a resist film to have a high planarity on the upper surface (resist side) of the film. High planarity means that the upper surface of the planarization film is formed horizontally. Further, if the planarity is high, the variation in the distance between the bottom face of the horizontally set substrate (the lowest substrate when a plurality of substrates is stacked) and the upper surface of the planarization film becomes small. The flat substrate means a substrate in which the distance between the bottom face and the upper surface of the substrate is substantially equal (in the substrate, the difference of the distance is 0-3% (μm)). The substrate which is not flat means, in a broad sense, a substrate which is not a flat substrate.

Figure 2:
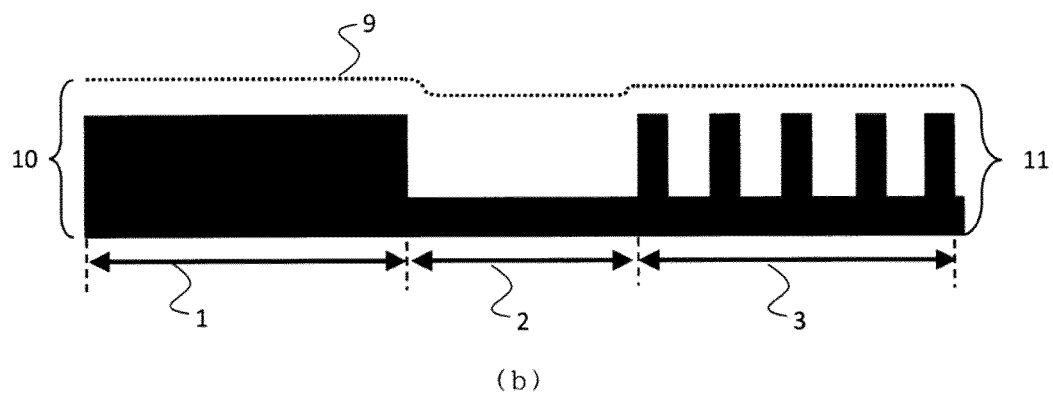
FIG. 2: Explanatory drawing of the structure of a substrate used for planarity evaluation

Hereinafter, the present invention is described using the drawings for understanding. The present inventors conducted study of Examples and Comparative Examples using the substrate shown in the drawing to obtain a composition capable of forming a film suitably even on a substrate having sparse and dense. Here, for the understanding of the invention, the scales of FIGS. 1 and 2 are not accurate. Reference numeral 1 denotes a land region, which has a width of 100 μm or more. Reference numeral 2 is a sea region, which has a width of 100 μm. Reference numeral 3 denotes a dense region, and a wall structure having a half pitch of 0.04 μm, a line space ratio of 1:2.5, and a depth of 100 nm exists in parallel with a width of 100 μm or more. The substrate is a $SiO_2$ wafer having enough depth. Reference numeral 4 denotes the bottom face of the substrate, and reference numeral 5 denotes the bottom portion of the substrate. When the substrate has a plurality of sea regions or trenches, as the height or distance in the present invention, a sea region or trench with the shortest distance to the bottom face is used (provided that a hole piercing through the substrate and a structure deviating from the intended design are excluded). Reference numeral 6 denotes the top portion of the substrate. When the substrate has a plurality of top portions or trenches, as the height or distance in the present invention, a top portion having the longest distance to the bottom face is used (provided that a structure deviating from the intended design is excluded). Reference numeral 7 denotes a height between the land region and the sea region and is the difference between the distance from the top portion to the bottom face of the land region and the distance from the bottom portion being in contact with the land region to the bottom face. Reference numeral 8 denotes a height between the dense region and the sea region and is the difference between the distance from the top portion of the dense region to the bottom face and the distance from the bottom portion being in contact with the dense region to the bottom face. The formed planarization film is in such a state as shown by reference numeral 9 in FIG. 2, and it is difficult to make the film completely flat (the distance from the bottom face is constant). Reference numeral 10 denotes a height from the bottom face of the substrate to the upper surface of the resist underlayer formed on the land region, and reference numeral 11 denotes a height from the bottom face of the substrate to the upper surface of the resist underlayer formed on the dense region. The resist underlayer forming composition found by the present inventors is suitable because even when a film is formed on a substrate that is not flat, the difference in height between 10 and 11 is small (high planarity). When evaluating the present composition, this difference is referred to as planarity.

In the present invention, the substrate which is not flat is a silicone-containing substrate in which the difference in height between the top portion of the substrate and the bottom portion of the substrate (that is, the difference between the distance from the top portion to the bottom face and the distance from the bottom portion to the bottom face) is 20-10,000 nm, preferably 50 to 1,000 nm, more preferably 50 to 500 nm. It is preferable to obtain this difference in the structure in which the top portion and the bottom portion are adjacent to each other as indicated by reference numerals 7 and 8. Further, as the substrate which is not flat, one having wall or a contact hole resulting from pretreatment can be referred, and one in which the difference between the distance from the top portion of the substrate to the bottom portion of the substrate and the distance from the bottom portion of the substrate to the bottom face of the substrate is 30-95% (µm) (preferably 30-80% (µm)) compared with the former can be also referred. The above-mentioned wall and contact hole can be formed by a known technique such as lithography, etching, DSA and the like, and those having an aspect ratio of 3-25 (preferably 5-10) are suitable. For example, a substrate in which wall structures are simply kept in parallel (see the region denoted by reference numeral 3 in FIG. 1) is also a substrate which is not flat, but when a (dense) region where such structures are gathered and a (sparse) region where they do not exist are unevenly distributed, usefulness of the present resist underlayer forming composition is exhibited. Furthermore, the flat film forming composition of the present invention can also be applied to a substrate having a step difference (see the regions of reference numerals 1 and 2 in FIG. 1). The step difference is preferably 20-10,000 nm, more preferably 50-1,000 nm, and further preferably 50-500 nm.

The resist underlayer of the present invention is applied on a flat substrate (bare wafer) and heated to form a film, and a film thickness of 20-2,000 nm (preferably 100-500 nm, more preferably 200-400 nm) can be obtained.

Regarding the substrate, as described above, a flat substrate and a non-flat substrate can be used, but the usefulness of the present invention can be exhibited more when a substrate that is not flat is used. As the substrate, a metal-containing substrate or a silicon-containing substrate can be used. The substrate in the present invention includes both a single-layer substrate and a lamination of a plurality of substrate layers. As the substrate, any known substrate such as a silicon-coated substrate, a silicon dioxide-coated substrate, a silicon nitride substrate, a silicon wafer substrate (such as $SiO_2$ wafer), a glass substrate, an indium-containing substrate (such as ITO substrate), a titanium-containing substrate (such as titanium nitride and titanium oxide) can be used.

In the process for manufacturing a semiconductor of the present invention, any known manner can be used for the layer structure of the substrate in accordance with the process conditions and, for example, the following laminated structure can be mentioned. In the following laminated structure, the left means the lower direction and the right means the upper direction.

Silicon wafer substrate
Silicon wafer substrate/titanium-containing substrate
Silicon wafer substrate/titanium-containing substrate/silicon-coated substrate
Silicon wafer substrate/titanium-containing substrate/silicon dioxide-coated substrate
Silicon wafer substrate/silicon dioxide-coated substrate/titanium-containing substrate
Silicon nitride substrate
Silicon nitride substrate/titanium-containing substrate
Silicon nitride substrate/titanium-containing substrate/silicon-coated substrate
Silicon nitride substrate/titanium-containing substrate/silicon dioxide-coated substrate
Silicon nitride substrate/silicon dioxide-coated substrate/titanium-containing substrate The other substrate to be laminated on any one of the substrates can be laminated using a known method such as CVD method. The other substrate can be patterned using a known lithography method or etching method. It is also possible to laminate another substrate on the patterned substrate by using a known method such as CVD method.

In the present invention, the resist underlayer forming composition of the present invention is coated by a suitable coating method such as a spinner, a coater or the like. The solid component of the composition according to the present invention is well in gap filling of the substrate since the solid component is the allyloxy derivative according to the present invention at the time of coating. In the coating of the resist underlayer forming composition on the substrate, it is preferable that the substrate and the resist underlayer forming composition come into direct contact with each other, but the resist underlayer forming composition may be coated via another thin film (for example, a substrate-modifying layer). After coating of the present composition, a resist underlayer is formed by ultraviolet radiation and/or heating. Preferably, curing of the composition according to the present invention is carried out by ultraviolet radiation or by ultraviolet radiation after heating.

As for the conditions of the ultraviolet irradiation after coating, it is preferable to irradiate ultraviolet radiation having a wavelength of 10-380 nm with an integrated irradiation amount of 100-10,000 $mJ/cm^2$. Thus, the allyloxy derivative according to the present invention is polymerized (cured) to obtain a resist underlayer. It is preferable when the wavelength is short (for example, 10 to 200 nm), because the self-cross-linking of the allyloxy derivative according to the present invention proceeds efficiently in this case, so the amount of the photopolymerization initiator can be reduced and film thickness uniformity of the formed resist underlayer is high. In the present specification, the film thickness uniformity means variation in thickness of a film formed by coating on a flat substrate and the high film thickness uniformity means that this variation is small. When the wavelength is long (for example, longer than 200 nm and not longer than 380 nm), curing can be performed efficiently by adding the photopolymerization initiator capable of absorbing the ultraviolet radiation to the composition according to the present invention.

The wavelength is preferably 10-200 nm, more preferably 100-200 nm, further preferably 125-195 nm, and even more preferably 170-175 nm. The integrated irradiation amount is preferably 100-5,000 $mJ/cm^2$, more preferably 200-1,000 $mJ/cm^2$, and further preferably 300-800 $mJ/cm^2$. Depending on the thickness of the resist underlayer to be formed, the above conditions can be appropriately modified.

In the case of curing the present resist underlayer by heating, as the heating condition, the heating temperature is appropriately selected from the range of 200-450° C. (preferably 225-375° C., more preferably 250-350° C.) and the heating time is appropriately selected from the range of 30-180 seconds (preferably 30 to 120 seconds). The heating can be divided into multiple steps (step baking). For example, the heating is carried out through two-step heating consisting of the first heating by which filling of the gaps in the substrate is performed while removing the solvent and the second heating by which the composition is lightly reflowed to form a film while securing planarity. For example, it is also preferable to perform the first heating at 200-300° C. for 30-120 seconds and the second heating at 300-400° C. for 30-120 seconds. Although the curing of the present resist underlayer forming composition may be carried out only by heating, combination of heating with ultraviolet radiation is also preferable. When the curing is carried out only by heating, it is preferable to add a cross-linking agent, an acid generator and/or a radical generator.

It is considered that the planarity is improved when a film is formed on a substrate which is not flat as a result of decrease of the glass transition temperature since the present allyloxy derivative has the group X.

As the atmosphere for irradiation with ultraviolet radiation and heating, air is suitable. The oxygen concentration can also be reduced to prevent oxidation of the present resist underlayer forming composition and the present resist underlayer. For example, the oxygen concentration may be adjusted to 1,000 ppm or less (preferably 100 ppm or less) by introducing an inert gas ($N_2$, Ar, He or any mixture of any of these) into the atmosphere.

By adding a further high-carbon material to the composition according to the present invention, etching resistance can be increased, and this is suitable as a resist underlayer formed by a spin on coating method. For the evaluation of the etching rate, a known method can be used, for example, a film having an etching rate of 1.0 or less as compared with a resist (UV1610, manufactured by Dow) is preferable, and a film having 0.9 or less is more preferable and a film having 0.8 or less is more preferable.

[Method of Forming Resist Film and Other Films]

A resist composition (for example, a positive-type resist composition) is applied on the resist underlayer formed as described above. Here, the positive-type resist composition refers to one which causes a reaction by being irradiated with light and increases the solubility of the irradiated region in a developing solution. Although the resist composition to be used is not particularly limited and any positive-type resist composition, a negative-type resist composition, or a negative tone development (NTD) resist composition can be used as long as it is sensitive to exposure light for pattern formation.

In the method of manufacturing a resist pattern of the present invention, presence of a film or layer other than the resist underlayer formed from the composition according to the present invention and a film or layer other than the resist film is also allowable. Further, a top anti-reflective coating (TARC layer) may be formed on the resist film.

In the process for manufacturing a semiconductor of the present invention, any known manner can be used for the layer structure other than the resist underlayer in accordance with the process conditions. When the resist underlayer is a planarization film, for example, the following laminated structure can be mentioned.

Substrate/planarization film/resist film

Substrate/planarization film/BARC layer/resist film

Substrate/planarization film/BARC layer/resist film/TARC layer

Substrate/planarization film/inorganic hard mask interlayer/resist film/TARC layer Substrate/planarization film/inorganic hard mask interlayer/BARC layer/resist film/TARC layer Substrate/planarization film/adhesive film/BARC layer/resist film/TARC layer Substrate/substrate-modifying layer/planarization film/BARC layer/resist film/TARC layer Substrate/substrate-modifying layer/planarization film/adhesive film/BARC layer/resist film/TARC layer These layers can be cured by heating and/or exposure after being coating, or can be formed by a known method such as CVD method. These layers can be removed by a known method (such as etching) and can be respectively patterned using an upper layer as a mask.

In one embodiment of the present invention, a resist underlayer can be formed on a non-flat substrate and another substrate can be formed thereon. For example, another substrate can be formed by a method such as CVD. The composition of the lower substrate and the upper substrate may be identical to or different from each other. Further, another layer can be formed on the upper substrate. Forming the resist underlayer and/or the resist film as this other layer enables processing of the upper substrate. The usable resist film and other films are the same as described above.

The resist film is exposed through a predetermined mask. The wavelength of the light to be used for exposure is not particularly limited, but it is preferable to perform the exposure with light having a wavelength of 13.5-248 nm. In particular, KrF excimer laser (wavelength: 248 nm), ArF excimer laser (wavelength: 193 nm), extreme ultraviolet (wavelength: 13.5 nm) and the like can be used, and KrF excimer laser is more preferred. These wavelengths allow a range of ±1% (nm). After the exposure, post exposure bake may be performed, if necessary. The temperature for the post exposure bake is selected from the range of 80-150° C., preferably 100 to 140° C., and the heating time is selected from the range of 0.3-5 minutes, preferably 0.5-2 minutes.

Next, development is performed with a developing solution. When a positive-type resist composition is used, the exposed region of the positive-type resist layer is removed by the development and a resist pattern is formed. This resist pattern can be further miniaturized using a shrink agent or the like.

Preferred as the developing solution to be used for the development in the resist pattern forming method is a 2.38 mass % (+−1% concentration accepted) TMAH aqueous solution. Using such a developing solution, it is possible to easily dissolve and remove the resist underlayer at room temperature. Further, a surfactant or the like can be added to the developing solution. The temperature of the developing solution is generally selected from the range of 5-50° C., preferably 25-40° C., and the development time is generally selected from the range of 10-300 seconds, preferably 30-60 seconds.

Using the obtained resist pattern as a mask, the interlayer can be patterned. For the pattern formation, a known method such as etching (dry etching, wet etching) and the like can be used. For example, a pattern can be formed on a substrate by etching the interlayer using the resist pattern as an etching mask and then etching the resist underlayer and the substrate using the obtained interlayer pattern as an etching mask. In another embodiment, a pattern can be formed on a substrate by etching the inorganic hard mask interlayer using the resist pattern as an etching mask, etching the resist underlayer using the obtained inorganic hard mask interlayer pattern as an etching mask, and then etching the substrate using the obtained resist underlayer pattern as an etching mask. Wiring can be formed on the substrate using the formed pattern.

For example, the present resist underlayer can be removed preferably by dry etching with $O_2$, $CF_4$, $CHF_3$, $Cl_2$ or $BCl_3$, preferably $O_2$ or $CF_4$.

Thereafter, if necessary, the substrate is further processed to form a device. For these further processing, well-known methods can be applied. After forming the device, if necessary, the substrate is cut into chips, which are connected to a lead frame, and packaged with resin. In the present invention, this packaged product is referred to as a device. The device preferably includes a semiconductor, a solar cell, an organic EL device, and an inorganic EL device, and a semiconductor is more preferable.

Hereinafter, the present invention is described with reference to examples. These examples are provided only for illustrative purpose and not intended to limit the scope of the present invention.

In the following description, "part" is on a mass basis unless otherwise specified.

Synthesis Example 1: P1

A reactor equipped with a stirrer, a condenser, a heating device, a nitrogen introducing pipe and a temperature controlling device was prepared. 9-fluorenone (200 parts, manufactured by Tokyo Chemical Industry Co., Ltd.), 9,9-bis(4-hydroxyphenyl)fluorene (2,333 parts, manufactured by Osaka Gas Chemicals Co., Ltd.) and dichloromethane (10, 430 parts) were added into the reactor and kept at 40° C. in a nitrogen atmosphere while stirring. Thereafter, trifluoromethanesulfonic acid (92 parts, manufactured by Mitsubishi Material Electronic Chemicals Co., Ltd.) and 3-mercaptopropionic acid (6 parts, manufactured by Tokyo Chemical Industry Co., Ltd.) dissolved in dichloromethane (200 parts) were slowly added into the reactor and subjected to the reaction for 4 hours while maintaining at 40° C. with stirring. After completion of the reaction, the solution was returned to room temperature, water was added to the reaction solution, excessive 9,9-bis(4-hydroxyphenyl)fluorene was removed by filtration and washed with dichloromethane. The dichloromethane solution was thoroughly washed with water to remove trifluoromethanesulfonic acid. Thereafter, dichloromethane was evaporated at 40° C. and 10 mmHg to obtain P1 precursor (2,111 parts). When the molecular weight was measured with GPC (tetrahydrofuran), the number-average molecular weight Mn was 533 Da, the weight-average molecular weight Mw was 674 Da, and the molecular weight distribution (Mw/Mn) was 1.26.

Next, a reactor equipped with a stirrer, a condenser, a heating device, a nitrogen introducing pipe and a temperature controlling device was prepared. P1 precursor (350 parts), potassium carbonate (562 parts) and acetone (1,414 parts) were added into the reactor and kept at 56° C. in a nitrogen atmosphere while stirring. Thereafter, allyl bromide (500 parts, manufactured by Tokyo Chemical Industry Co., Ltd.) was slowly added into the reactor and subjected to the reaction for 3 hours while maintaining at 56° C. with stirring. After completion of the reaction, the solution was returned to room temperature, excess potassium carbonate and its salt were removed by filtration and the precipitate was washed with acetone. Thereafter, acetone was evaporated at 40° C. and 10 mmHg. The obtained solid matter was dissolved in ethyl acetate (3,000 parts), and the ethyl acetate solution was thoroughly washed with water to remove metal impurities. Ethyl acetate was evaporated at 40° C. and 10 mmHg, and thereafter the obtained solid content was dissolved in acetone (600 parts). Thereafter, the acetone solution was poured into n-heptane (6,000 parts), the solid matter was filtered and dried under the condition of 100° C. and 10 mmHg to obtain P1 (345 parts). When the molecular weight was measured with GPC (tetrahydrofuran), the number average-molecular weight Mn was 671 Da, the weight-average molecular weight Mw was 833 Da, and the molecular weight distribution (Mw/Mn) was 1.32.

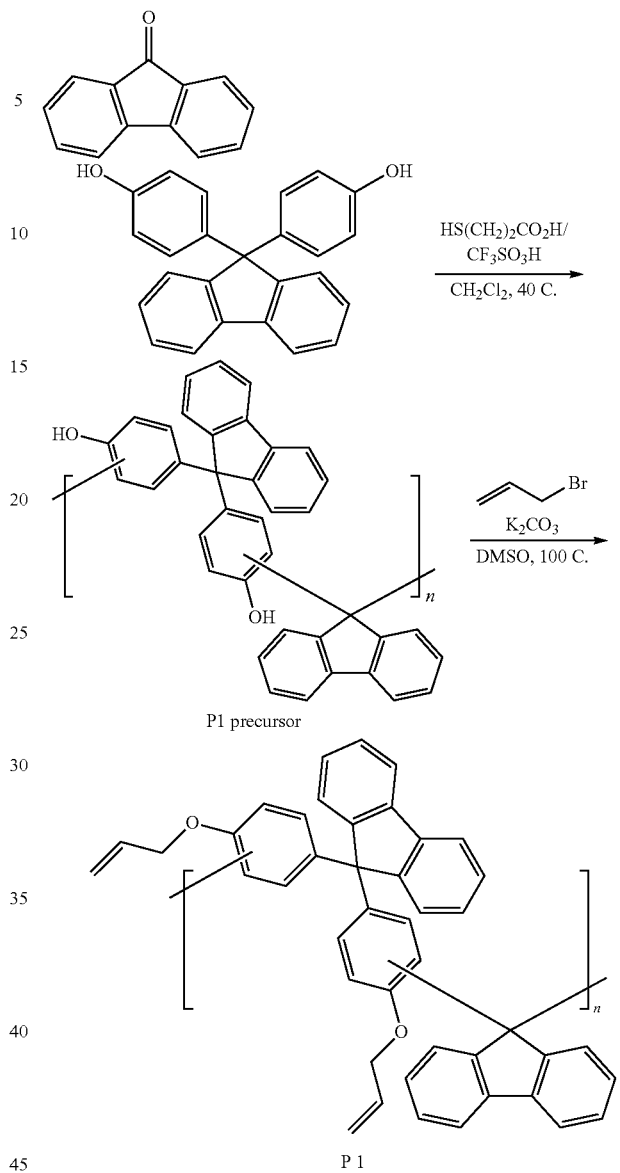

Synthesis Example 2: P2

A reactor equipped with a stirrer, a condenser, a heating device, a nitrogen introducing pipe and a temperature controlling device was prepared. TPBC (manufactured by Toyo Gosei Co., Ltd.) (10 parts), potassium carbonate (28 parts) and dimethylsulfoxide (65 parts) were added into the reactor and kept at 100° C. in a nitrogen atmosphere while stirring. Thereafter, allyl bromide (25 parts) was slowly added into the reactor and subjected to the reaction for 3 hours while maintaining at 100° C. with stirring. After completion of the reaction, the solution was returned to room temperature and poured into pure water (200 parts). Using a filter paper, the solid matter was filtered from this liquid. The obtained solid matter was dissolved in ethyl acetate (100 parts) and the ethyl acetate solution was thoroughly washed with water to remove metal impurities. Ethyl acetate and excessive allyl bromide were evaporated at 40° C. and 10 mmHg to obtain P2 (12 parts).

P2 was analyzed by NMR. The results were as shown below, and it was confirmed that P2 had the following structure.

$^1$H-NMR (400 MHz in DMSO-d6): 7.30-7.10 (d, 8H, Ph), 6.90-6.70 (d, 8H, Ph), 6.00 (m, 4H, CH$_2$=C$\underline{H}$CH$_2$), 5.40-5.20 (m, 8H, C$\underline{H_2}$=CHCH$_2$), 4.50 (d, 8H, CH$_2$=CHC$\underline{H_2}$O), 2.70-1.00 (m, 20H, cyclohexyl), 0.40 (s, 6H, C$\underline{H_3}$)

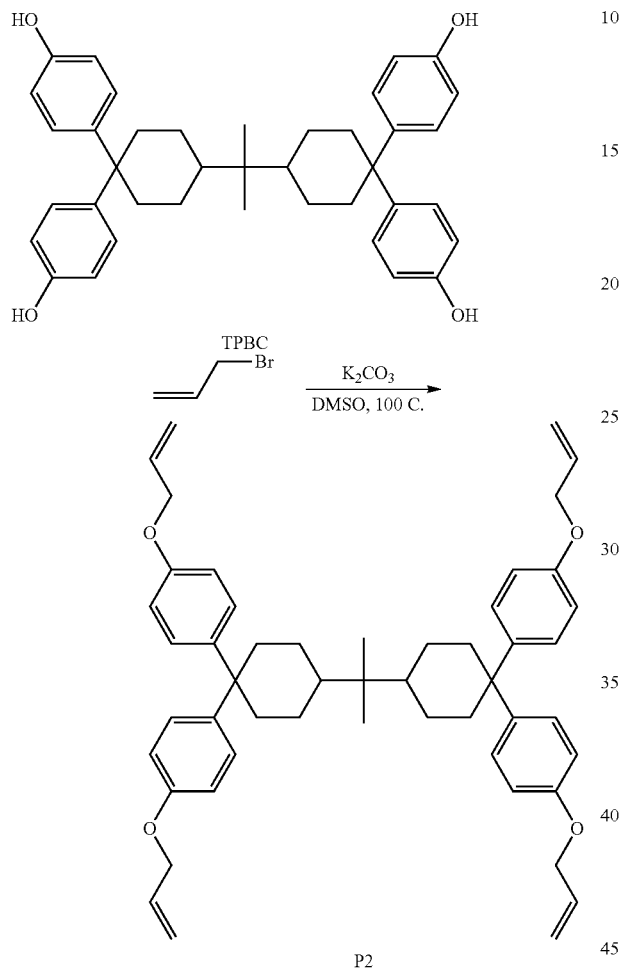

Synthesis Example 3: P3

A reactor equipped with a stirrer, a condenser, a heating device, a nitrogen introducing pipe and a temperature controlling device was prepared. BIP-ANT (manufactured by Asahi Yukizai Corporation) (10 parts), potassium carbonate (22 parts) and dimethyl sulfoxide (51 parts) were added into the reactor and kept at 100° C. in a nitrogen atmosphere while stirring. Thereafter, allyl bromide (19 parts) was slowly added into the reactor and subjected to the reaction for 3 hours while maintaining at 100° C. with stirring. After completion of the reaction, the solution was returned to room temperature and poured into pure water (200 parts). Using a filter paper, the solid matter was filtered from this liquid. The obtained solid matter was dissolved in ethyl acetate (100 parts), and the ethyl acetate solution was thoroughly washed with water to remove metal impurities. Ethyl acetate was evaporated at 40° C. and 10 mmHg, and the obtained solid matter was dissolved in ethyl acetate (25 parts). Thereafter, the ethyl acetate solution was poured into n-heptane (120 parts), the solid matter was filtered and dried at 50° C. and 10 mmHg to obtain P3 (11 parts).

P3 was analyzed by NMR. The results were as shown below, and it was confirmed that P3 had the following structure.

$^1$H-NMR (400 MHz in DMSO-d6): 8.37-7.38 (m, 8H, Anthryl-$\underline{H}$), 7.30-6.79 (m, 8H, Ph), 6.15-5.94 (m, 2H, CH$_2$=C$\underline{H}$CH$_2$), 5.51-5.18 (m, 4H, C$\underline{H_2}$=CHCH$_2$), 4.99 (s, 2H, Ph-C$\underline{H_2}$-Anthryl), 4.70, 4.44 (d, J=2.4 Hz, 2.6 Hz, CH$_2$=CHC$\underline{H_2}$O)

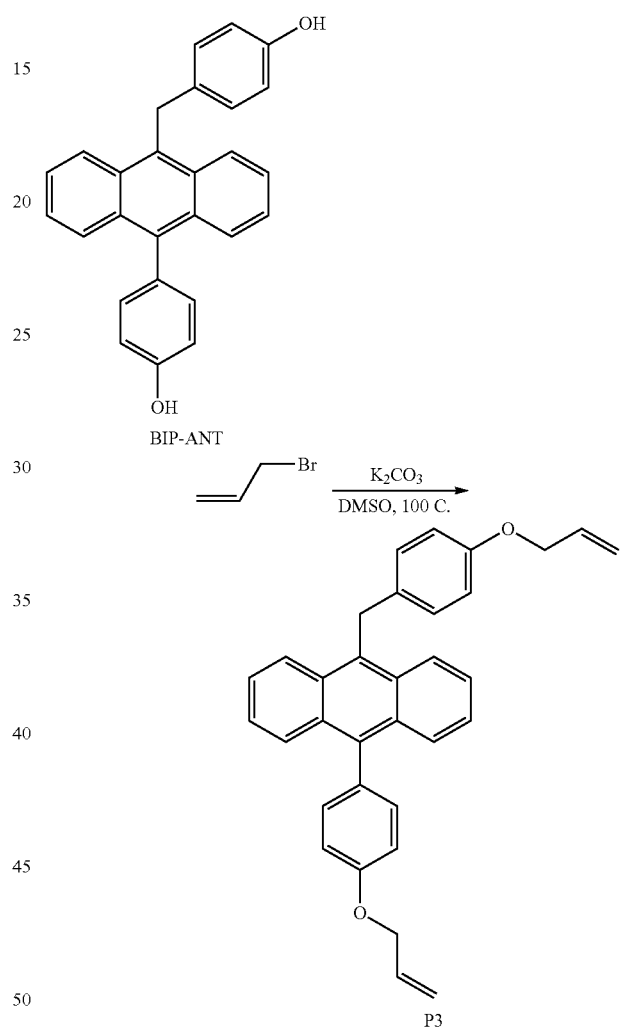

Synthesis Example 4: P4

A reactor equipped with a stirrer, a condenser, a heating device, a nitrogen introducing pipe and a temperature controlling device was prepared. Tek25X-MBSA (Honshu Chemical Industry Co., Ltd.) (10 parts), potassium carbonate (35 parts) and dimethylsulfoxide (77 parts) were added into the reactor and kept at 100° C. in a nitrogen atmosphere while stirring. Thereafter, allyl bromide (31 parts) was slowly added into the reactor and subjected to the reaction for 3 hours while maintaining at 100° C. with stirring. After completion of the reaction, the same impurity removing operation as in Synthesis Example 3 was performed to obtain P 4 (13 parts).

The NMR results of P4 were as shown below, and it was confirmed that P4 had the following structure.

¹H-NMR (400 MHz in DMSO-d6): 6.83 (s, 4H, Ph), 6.72 (s, 4H, Ph), 6.45 (s, 2H, Ph), 6.15-5.80 (m, 8H, CH$_2$=CHCH$_2$), 5.80 (s, 2H, PhCH(Ph)$_2$), 5.42-5.09 (m, 12H, CH$_2$=CHCH$_2$), 4.41-4.40 (m, 12H, CH$_2$=CHCH$_2$O), 3.57 (s, 2H, PhCH$_2$Ph), 2.01 (s, 12H, CH$_3$), 1.90 (s, 12H, CH$_3$)

obtained solid matter, and the excessive allyl bromide was washed. Thereafter, the solid matter was filtered and dried at 50° C. and 10 mmHg to obtain P5 (11 parts).

The NMR results of P5 were as shown below, and it was confirmed that P4 had the following structure.

¹H-NMR (400 MHz in DMSO-d6): 7.92-6.98 (m, 24H, Ph), 5.92 (m, 2H, CH$_2$=CHCH$_2$), 5.28-5.13 (m, 4H, CH$_2$=CHCH$_2$), 4.51 (d, J=2.0 Hz, 4H, CH$_2$=CHCH$_2$O)

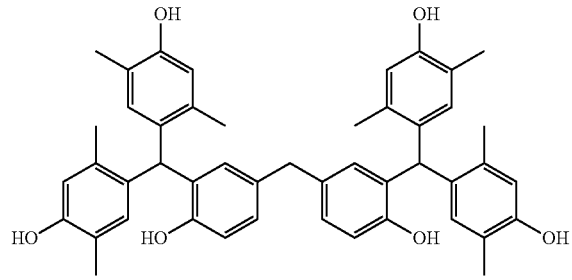

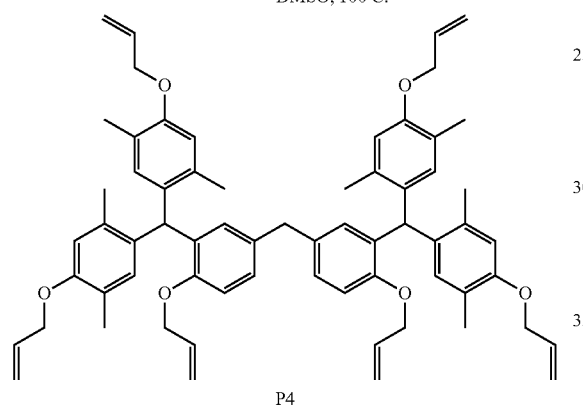

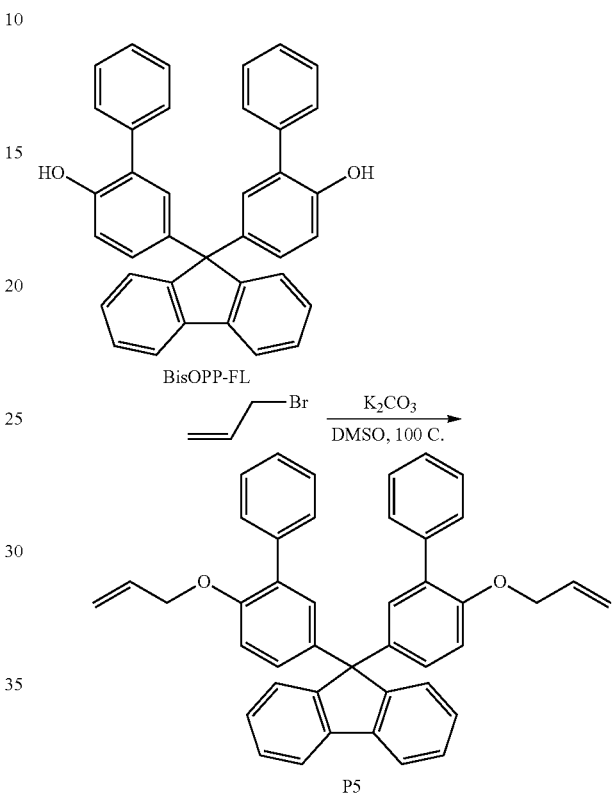

Synthesis Example 5: P5

A reactor equipped with a stirrer, a condenser, a heating device, a nitrogen introducing pipe and a temperature controlling device was prepared. BisOPP-FL (manufactured by Honshu Chemical Industry Co., Ltd.) (10 parts), potassium carbonate (16 parts) and dimethylsulfoxide (41 parts) were added into the reactor and kept in a nitrogen atmosphere while stirring. Thereafter, allyl bromide (14 parts) was slowly added into the reactor and subjected to the reaction for 3 hours while maintaining at 100° C. with stirring. After completion of the reaction, the solution was returned to room temperature and poured into pure water (200 parts). Using a filter paper, the solid matter was filtered from this liquid. Ethyl acetate (100 parts) was added to the Preparation Example 1: Composition 1

Propylene glycol 1-monomethyl ether 2-acetate (PG-MEA) (2,500 parts) was added to P1 (100 parts) and filtration was conducted through a fluororesin filter (SLFG025NS, manufactured by Merck Millipore) of 0.2 μm to obtain Composition 1.

Preparation Examples 2-7: Compositions 2-7

Compositions 2-7 were prepared in the same manner as in Preparation Example 1 except that the components were changed as shown in Table 1 below.

TABLE 1

|  | Allyloxy derivative | Cross-kinking agent | Additive 1 | Additive 2 | Solvent |
| --- | --- | --- | --- | --- | --- |
| Preparation Example 1 | Compositon 1 P1 (100 parts) | — | — | — | PGMEA (2500 parts) |
| Preparation Example 2 | Compositon 2 P1 (100 parts) | TM-BIP-ANT (20 parts) | — | — | PGMEA (2500 parts) |
| Preparation Example 3 | Compositon 3 P1 (100 parts) | HM-HAP (20 parts) | — | — | PGMEA (2500 parts) |

TABLE 1-continued

| | | Allyloxy derivative | Cross-kinking agent | Additive 1 | Additive 2 | Solvent |
|---|---|---|---|---|---|---|
| Preparation Example 4 | Compositon 4 | P2 (100 parts) | — | — | — | PGMEA (2500 parts) |
| Preparation Example 5 | Compositon 5 | P3 (100 parts) | — | — | — | PGMEA (2500 parts) |
| Preparation Example 6 | Compositon 6 | P4 (100 parts) | — | — | — | PGMEA (2500 parts) |
| Preparation Example 7 | Compositon 7 | P5 (100 parts) | — | — | — | Cyclopentanone (2500 parts) |
| Comparative Peparation Example 1 | Comparative Composition 1 | FW352 (100 parts) | — | Triphenylsulfonium Trifluorometh-anesulfonate (5 parts) | MEGAFAC R-30* (1 parts) | PGMEA(2500 parts) |
| Comparative Peparation Example 2 | Comparative Composition 2 | P1 precursor (100 parts) | — | — | — | PGMEA (2500 parts) |
| Comparative Peparation Example 3 | Comparative Composition 3 | P6 (100 parts) | — | — | — | PGMEA (2500 parts) |

In the table,
*MEGAFAC R-30 (DIC Corporation)
Chemical structural formulas other than the already shown above are as follows.

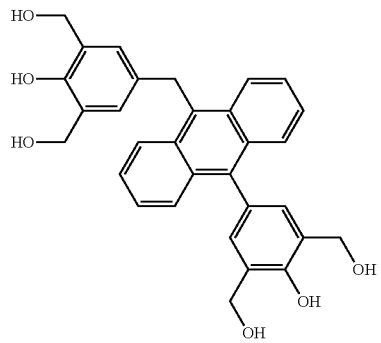

TM-BIP-ANT (Asahi Yukizai Corporation)

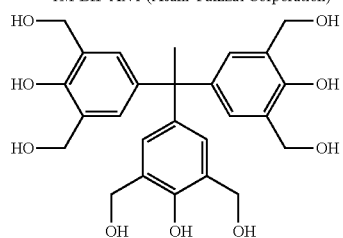

HM-HAP (Asahi Yukizai Corporation)

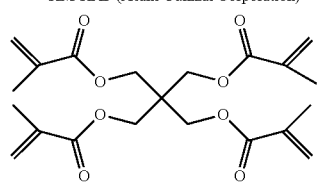

FW352 (Sigma-Aldrich)

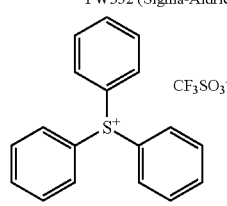

Triphenylsulfonium Trifluoromethanesulfonate (Midori Kagaku Co., Ltd.)

TABLE 1-continued

| | Allyloxy derivative | Cross-kinking agent | Additive 1 | Additive 2 | Solvent |
|---|---|---|---|---|---|

P6 (disclosed in JP5794228B)

[Evaluation of Weight Reduction Rate]

Using CLEAN TRACK ACT 12 (manufactured by Tokyo Electron Limited), Compositions 1-7 and Comparative Compositions 1-3 were respectively applied on a Si bare wafer at 1,500 rpm. The wafer was baked in an air atmosphere at 320° C. for 90 seconds and then irradiated with vacuum ultraviolet radiation (VUV) of 172 nm at 1,000 mJ/cm$^2$. Further, the wafer was baked at 400° C. for 60 seconds under an air atmosphere. The film was scraped off and, using Thermo plus EV02 (manufactured by Rigaku Corporation), it was heated to 400° C. at 20° C./min in air and the weight change was measured. The difference in the sample weight between before the temperature rises and after raising the temperature to 400° C. was taken as the weight reduction rate (%). The obtained results were as shown in Table 2 below. The weight reduction ratio of the films made from Comparative Composition 1 and Comparative Composition 3 were large.

TABLE 2

| | weight reduction rate (%) |
|---|---|
| Composition 1 | 4.2 |
| Composition 2 | 4.6 |
| Composition 3 | 4.7 |
| Composition 4 | 28.8 |
| Composition 5 | 11.0 |
| Composition 6 | 20.2 |
| Composition 7 | 6.8 |
| Comparative Composition 1 | 42.3 |
| Comparative Composition 2 | 4.3 |
| Comparative Composition 3 | 42.3 |

[Evaluation of Film Thickness Reduction Rate]

Using CLEAN TRACK ACT 12, Compositions 1-3 and Comparative Compositions 1-3 were respectively applied on a Si bare wafer at 1,500 rpm. The wafer was baked in an air atmosphere at 320° C. for 90 seconds and then irradiated with vacuum ultraviolet radiation (VUV) of 172 nm at 1,000 mJ/cm$^2$ to form a film. The thickness of the film on the wafer was measured with a LAMBDA ACE VM-3110 type spectroscopic reflectometer film thickness measurement system (manufactured by SCREEN Holdings Co., Ltd.), and this was taken as A nm. Further, the wafer was baked at 400° C. for 60 seconds under an air atmosphere. The thickness of the film being on the wafer was measured with the LAMBDA ACE, and this was taken as B nm. The film thickness reduction ratio of before and after baking at 40° C. for 60 seconds was calculated by 100−B/A×100. The obtained results were as shown in Table 3 below. The composition according to the present invention showed less film thickness reduction ratio even after high temperature baking (400° C. for 60 seconds).

[Evaluation of Planarity]

Using MS-150A type spin coater (manufactured by Mikasa Co., Ltd.), Compositions 1-3 and Comparative Compositions 1-3 were respectively applied at 1,500 rpm on a SiO$_2$ wafer (substrate not being flat) shown in FIG. 1 to bring the state that the sea region of the substrate and the trenches between the walls of the dense region were filled and the land region was covered with the composition. This film was baked in an air atmosphere at 320° C. for 90 seconds and then irradiated with vacuum ultraviolet radiation (VUV) of 172 nm at 1,000 mJ/cm$^2$. This was baked in an air atmosphere at 400° C. for 60 seconds to obtain a planarization film 1. To evaluate the planarity of the planarization film 1, planarity (difference in height between reference numerals 11 and 12 in FIG. 2) was measured with images of SEM (S-5500, manufactured by Hitachi High-Tech Fielding Corporation). The obtained results were as shown in Table 3 below. Even when the composition according to the present invention was applied on a non-flat substrate to form a film, it was possible to form a film with high planarity.

TABLE 3

| | Film thickness A (nm) | Film thickness B (nm) | Film thickness reduction rate (%) (100 − B/A × 100) | Planarity (nm) |
|---|---|---|---|---|
| Composition 1 | 116 | 110 | 5.2 | 8 |
| Composition 2 | 118 | 111 | 5.9 | 9 |
| Composition 3 | 117 | 110 | 6.0 | 9 |
| Comparative Composition 1 | 118 | 21 | 82.2 | 78 |
| Comparative Composition 2 | 114 | 108 | 5.3 | 45 |
| Comparative Composition 3 | 118 | 29 | 75.4 | 79 |

1. Land region of substrate
2. Sea region of substrate
3. Dense region of substrate
4. Bottom face of substrate
5. Bottom portion of substrate
6. Top portion of substrate
7. Height between land region and sea region
8. Height between dense region and sea region
9. Formed planarization film
10. Height between top portion of land region and bottom face of substrate
11. Height between top portion of dense region and bottom face of substrate

The invention claimed is:

1. A resist underlayer forming composition comprising: an allyloxy derivative comprising a group X represented by the following formula (1):

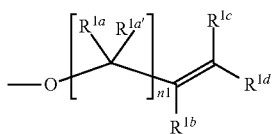

wherein, $R^{1a}$ and $R^{1a'}$ are each independently hydrogen, or linear or branched $C_{1-4}$ alkyl, $R^{1b}$, $R^{1c}$, and $R^{1d}$, are each independently hydrogen, or linear or branched $C_{1-4}$ alkyl, and n1 is 1, 2, or 3; and a solvent and the number of atoms contained in one or more solid components of said resist underlayer forming composition satisfies the following formula:

$$1.5 \leq \{\text{total number of atoms/(number of C−number of O)}\} \leq 3.5,$$

where, the number of C is the number of carbon atoms in the total number of atoms, and the number of O is the number of oxygen atoms in the total number of atoms.

2. The composition according to claim 1, wherein said allyloxy derivative has three or more group X.

3. The composition according to claim 1, wherein said solvent is water, a hydrocarbon solvent, an ether solvent, an ester solvent, an alcohol solvent, a ketone solvent, or any mixture of any of these.

4. The composition according to claim 1, further comprising a surfactant, a cross-linking agent, an acid generator, a radical generator, a photopolymerization initiator, an agent for enhancing the adhesion to substrates, or any mixture of any of these.

5. The composition according to claim 1, wherein said resist underlayer forming composition comprises a cross-linking agent in a concentration of 0-300,000 ppm, a photopolymerization initiator in a concentration of 0-100,000 ppm, an acid generator in a concentration of 0-50,000 ppm, and/or a radical generator in a concentration of 0-50,000 ppm.

6. An allyloxy derivative comprising three or more group X represented by the following formula (1):

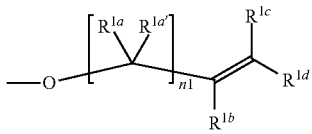

wherein, $R^{1a}$ and $R^{1a'}$ are each independently hydrogen, or linear or branched $C_{1-4}$ alkyl, $R^{1b}$, $R^{1c}$, and $R^{1d}$ are each independently hydrogen, or linear or branched $C_{1-4}$ alkyl, and n1 is 1, 2, or 3 and a structural unit represented by the following formula (4):

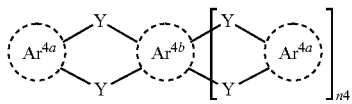

wherein, $Ar^{4a}$ and $Ar^{4b}$ are each independently a $C_{6-10}$ aromatic hydrocarbon ring and each $Ar^{4a}$ can be identical to or different from each other, n4 is 0, 1, or 2, Y is each independently a single bond or $C_{1-9}$ alkylene, and at least one Y contained in the formula is a substituted methylene group which bonds to the other portion of the allyloxy derivative, and with the proviso that $Ar^{4a}$ and $Ar^{4b}$ are not bonded with each other by two single bonds.

7. The composition according to claim 1, wherein the allyloxy derivative further comprises a structural unit of formula (5):

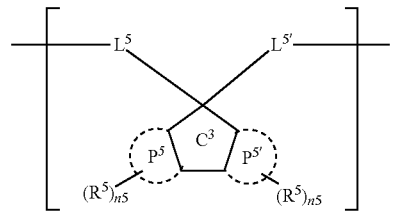

wherein, $p^5$ and $p^{5'}$ are each independently a $C_{6-10}$ aromatic hydrocarbon ring and each of said $p^5$ and $p^{5'}$ contains two adjacent carbon atoms in cs as constitution atoms, $R^5$ is each independently $C_{1-6}$ alkyl, halogen, or cyano, n5 is each independently 0, 1, 2, 3, or 4, $L^5$ is each independently a single bond or $C_{1-9}$ alkylene, and $L^{5'}$ is each independently a single bond, $C_{1-9}$ alkylene, or hydrogen.

8. The composition according to claim 1, wherein the allyloxy derivative further comprises a structural unit represented by the following formula (2):

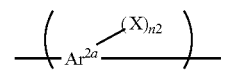

wherein, $Ar^{2a}$ is a $C_{6-40}$ aromatic hydrocarbon group, n2 is 1, 2, 3, or 4, and X is as defined in claim 6 and when n2 is 2, 3, or 4, X can be identical to or different from each other and a structural unit represented by the following formula (4):

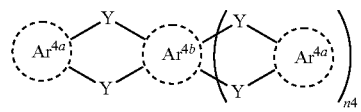

wherein, $Ar^{4a}$ and $Ar^{4b}$ are each independently a $C_{6-10}$ aromatic hydrocarbon ring and each $Ar^{4a}$ can be identical to or different from each other, n4 is 0, 1, or 2, Y is each independently a single bond or $C_{1-9}$ alkylene, and at least one Y contained in the formula is a substituted methylene group which bonds to the other portion of the allyloxy derivative, and with the proviso that $Ar^{4a}$ and $Ar^{4b}$ are not bonded with each other by two single bonds, wherein the ratio of the structural unit represented by the formula (2) is 30-95 mol % and the ratio of the structural unit represented by the formula (4) is 10-70 mol %, based on the all structural units of the allyloxy derivative.

9. A resist underlayer forming composition comprising:

an allyloxy derivative comprising a group X represented by the following formula (1):

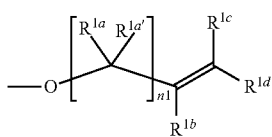

wherein, $R^{1a}$ and $R^{1a'}$ are each independently hydrogen, or linear or branched $C_{1-4}$ alkyl, $R^{1b}$, $R^{1c}$, and $R^{1d}$, are each independently hydrogen, or linear or branched $C_{1-4}$ alkyl, and n1 is 1, 2, or 3; and a solvent and wherein the content of said allyloxy derivative is 2-60 mass % based on the total mass of said resist underlayer forming composition.

10. A method of manufacturing a resist underlayer comprising:

applying the composition according to claim 1 above a substrate to form a resist underlayer forming composition layer; and curing said resist underlayer forming composition layer.

11. The method according to claim 10, wherein the curing of said resist underlayer forming composition is performed by irradiating with ultraviolet radiations having a wavelength of 10-380 nm.

12. The method according to claim 10, wherein the curing of said resist underlayer forming composition is performed by heating at 200-450° C.

13. A method of manufacturing a semiconductor device comprising:

manufacturing the resist underlayer according to claim 10;

applying a resist composition above said resist underlayer to form a resist composition layer;

exposing said resist composition layer;

developing said resist composition layer after the exposure to form a resist pattern;

etching with said resist pattern as a mask; and processing the substrate.

14. The method according to claim 13, further comprising forming wiring in the processed substrate.

15. The composition according to claim 1, wherein the allyloxy derivative further comprises a structural unit represented by the formula (3)

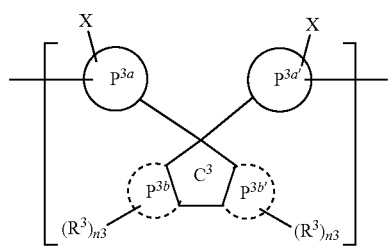

wherein, $p^{3a}$ and $p^{3a'}$ are each independently a $C_{6-10}$ aromatic hydrocarbon ring, $p^{3b}$ and $p^{3b'}$ are each independently a $C_{6-10}$ aromatic hydrocarbon ring and each of said $p^{3b}$ and $p^{3b'}$ contains two adjacent carbon atoms in $C^3$ as constitution atoms, $R^3$ is each independently $C_{1-6}$ alkyl, halogen, or cyano, n3 is each independently 0, 1, 2, 3, or 4, and X is as defined in claim 6 and can be identical to or different from each other.

16. The allyloxy derivative according to claim 6, wherein the portion other than the group X constituting said allyloxy derivative is selected from linear or branched alkyl, a saturated hydrocarbon ring, an aromatic hydrocarbon ring, or any combination of any of these, and the number of carbon atoms of said portion other than the group X is 6 or more.

17. The allyloxy derivative according to claim 6, comprising a structural unit represented by the following formula (2):

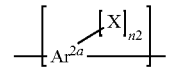

wherein, $Ar^{2a}$ is a $C_{6-40}$ aromatic hydrocarbon group, n2 is 1, 2, 3, or 4, and X is as defined in claim 6 and when n2 is 2, 3, or 4, X can be identical to or different from each other.

18. The allyloxy derivative according to claim 17, wherein the structural unit represented by the formula (2) is a structural unit represented by the following formula (3):

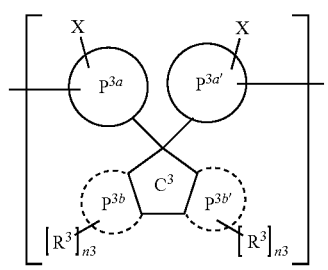

wherein, $p^{3a}$ and $p^{3a'}$ are each independently a $C_{6-10}$ aromatic hydrocarbon ring, $p^{3b}$ and $p^{3b'}$ are each independently a $C_{6-10}$ aromatic hydrocarbon ring and each of said $p^{3b}$ and $p^{3b'}$ contains two adjacent carbon atoms in $C^3$ as constitution atoms, $R^3$ is each independently $C_{1-6}$ alkyl, halogen, or cyano, n3 is each independently 0, 1, 2, 3, or 4, and X is as defined in claim 6 and can be identical to or different from each other.

19. The allyloxy derivative according to claim 17, wherein the ratio of the structural unit represented by the formula (2) is 30-95 mol % and the ratio of the structural unit represented by the formula (4) is 10-70 mol %, based on the all structural units of said allyloxy derivative.

20. The allyloxy derivative according to claim 6, wherein the structural unit represented by the formula (4) is a structural unit represented by the following formula (5):

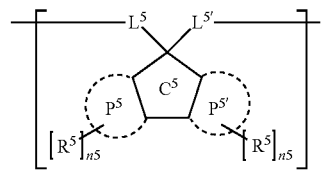
(5)

wherein, $p^5$ and $p^{5'}$ are each independently a $C_{6-10}$ aromatic hydrocarbon ring and each of said $p^5$ and $p^{5'}$ contains two adjacent carbon atoms in cs as constitution atoms, $R^5$ is each independently $C_{1-6}$ alkyl, halogen, or cyano, n5 is each independently 0, 1, 2, 3, or 4, $L^5$ is each independently a single bond or $C_{1-9}$ alkylene, and $L^{5'}$ is each independently a single bond, $C_{1-9}$ alkylene, or hydrogen.

* * * * *